United States Patent
Herman et al.

(10) Patent No.: US 10,627,374 B2
(45) Date of Patent: *Apr. 21, 2020

(54) LC-MS CONFIGURATION FOR PURIFICATION AND DETECTION OF ANALYTES HAVING A BROAD RANGE OF HYDROPHOBICITES

(71) Applicant: COHESIVE TECHNOLOGIES INC., Franklin, MA (US)

(72) Inventors: Joseph L. Herman, West Chester, PA (US); Robert Dewitte, Burlington (CA); Dayana Argoti, Charlestown, MA (US)

(73) Assignee: Cohesive Technologies Inc., Franklin, MA (US)

(*) Notice: Subject to any disclaimer, the term of this patent is extended or adjusted under 35 U.S.C. 154(b) by 235 days.

This patent is subject to a terminal disclaimer.

(21) Appl. No.: 15/445,826

(22) Filed: Feb. 28, 2017

(65) Prior Publication Data

US 2017/0168029 A1 Jun. 15, 2017

Related U.S. Application Data

(63) Continuation of application No. 13/881,848, filed as application No. PCT/US2011/058430 on Oct. 28, 2011, now Pat. No. 9,625,429.

(Continued)

(51) Int. Cl.
*G01N 30/72* (2006.01)
*G01N 30/88* (2006.01)
(Continued)

(52) U.S. Cl.
CPC ......... *G01N 30/7233* (2013.01); *G01N 30/34* (2013.01); *G01N 30/88* (2013.01);
(Continued)

(58) Field of Classification Search
CPC .......... G01N 30/7233; G01N 33/9493; G01N 33/82; G01N 30/34; G01N 30/88;
(Continued)

(56) References Cited

U.S. PATENT DOCUMENTS

| 5,772,874 A | 6/1998 | Quinn et al. |
| 5,795,469 A * | 8/1998 | Quinn .................. B01D 15/163 |
| | | 210/198.2 |

(Continued)

FOREIGN PATENT DOCUMENTS

| EP | 1074836 | 2/2001 |
| JP | H269657 | 3/1990 |

(Continued)

OTHER PUBLICATIONS

Herman, Generic approach to high throughput ADME screening for lead candidate optimization.pdf (Year: 2003).*

(Continued)

*Primary Examiner* — Randy W Gibson
*Assistant Examiner* — Gedeon M Kidanu
(74) *Attorney, Agent, or Firm* — Workman Nydegger

(57) ABSTRACT

Systems, apparatuses, kits, and methods for purification and analysis of analytes having a broad range of hydrophobicities by liquid chromatography-mass spectrometry (LC-MS). Using one set of liquid chromatography columns, one set of mobile phase buffers, and, optionally, a single ionization method (e.g., electrospray ionization), a wide range of analytes can be purified and analyzed on a liquid chromatography-mass spectrometry (LC-MS) system. LC-MS purification and analysis of analytes having a broad range of partition coefficients is accomplished by selecting LC run parameters and MS system parameters that are particular to different classes of analytes without having to make column or buffer changes or any other hardware configuration (Continued)

changes to the LC-MS system. The methods, systems, and kits described herein provide for substantially increased speed/throughput and ease of use for a wide range analytes with essentially no compromise in specificity for individual analytes relative to previously described methods.

37 Claims, 26 Drawing Sheets

Related U.S. Application Data

(60) Provisional application No. 61/408,266, filed on Oct. 29, 2010.

(51) Int. Cl.
| | |
|---|---|
| *G01N 33/68* | (2006.01) |
| *G01N 30/34* | (2006.01) |
| *G01N 33/82* | (2006.01) |
| *G01N 33/94* | (2006.01) |
| *G01N 30/32* | (2006.01) |

(52) U.S. Cl.
CPC ......... *G01N 33/6848* (2013.01); *G01N 33/82* (2013.01); *G01N 33/9493* (2013.01); *G01N 30/32* (2013.01); *G01N 2030/8813* (2013.01); *G01N 2430/00* (2013.01)

(58) Field of Classification Search
CPC ............... G01N 33/6848; G01N 30/32; G01N 2030/8813; G01N 2430/00
See application file for complete search history.

(56) References Cited

U.S. PATENT DOCUMENTS

| | | | |
|---|---|---|---|
| 5,919,368 A | 7/1999 | Quinn et al. | |
| 5,968,367 A | 10/1999 | Quinn et al. | |
| 6,207,954 B1* | 3/2001 | Andrien, Jr. | H01J 9/0009 250/282 |
| 8,414,774 B2* | 4/2013 | LaMarr | G01N 30/24 210/141 |
| 2010/0155594 A1 | 6/2010 | Goldman et al. | |
| 2013/0288355 A1* | 10/2013 | DeWitte | G01N 30/06 435/288.6 |
| 2014/0047906 A1 | 2/2014 | Herman | |
| 2014/0147878 A1* | 5/2014 | Herman | G01N 33/82 435/29 |

FOREIGN PATENT DOCUMENTS

| | | |
|---|---|---|
| JP | 9229920 | 9/1997 |
| JP | 2001124756 | 5/2001 |
| JP | 2008261754 | 10/2008 |
| WO | 2008046045 | 4/2008 |
| WO | 2012058619 | 5/2012 |

OTHER PUBLICATIONS

Herman, Generic approach to high throughput ADME screening for lead candidate optimization (Year: 2003).*

International Search Report and Written Opinion for PCT/US2011/058430 dated Mar. 2, 2012.
Gracia-Lor et al. "Simultaneous Determination of Acidic, Neutral and Basic Pharmaceuticals for Urban Wastewater by Ultra High-Pressure Liquid Chromatography-Tandem Mass Spectrometry," Journal of Chromatography, Jan. 2010, vol. 1217, No. 5, p. 622-632.
Gros et al. "Development of a Multi-Residue Analytical Methodology Based on Liquid Chromatography-Tandem Mass Spectrometry (LC-MS/MS) for Screening and Pharmaceuticals in Surface and Wastewaters," Talanta, Nov. 2006, vol. 70, No. 4, p. 678-690.
Herman, "Generic Approach to High Throughput ADME Screening for Lead Candidate Optimization," International Journal of Mass Spectrometry, Nov. 2004, vol. 238, No. 2, p. 107-117.
Herman, "Generic Method for On-Line Extraction of Drug Substances in the Presence of Biological Matrices Using Turbulent Flow Chromatography," Rapid Communications in Mass Spectrometry, 2002, vol. 16, pp. 421-426.
Lan Gao et al. "A Generic Fast Solid-Phase Extraction High-Performance Liquid Chromatography/Mass Spectrometry Method for High-Throughput Drug Discovery," Rapid Communications in Mass Spectrometry, Nov. 2007, vol. 21, No. 21, p. 3497-3504.
Maunsell et al. "Routine Isotope-Dilution Liquid Chromatography-Tandem Mass Spectrometry Assay for Simultaneous Measurement of the 25 Hydroxy Metabolites of Vitamins D2 and D3," Cinical Chemistry, American Association for Clinical Chemistry, Washington DC, 2005, vol. 51, No. 9, p. 1683-1690.
Maurer, "Multi-Analte Procedures for Screening for and Quantification of Drugs in Blood, Plasma, or Serum by Liquid Chromatography-Single Stage or Tandem Mass Spectrometry (LC-MS/MS) Relevant to Clinical and Forensic Toxicology," Clinical Biochestry, Apr. 2005, vol. 38, No. 4, p. 310-318.
Salm et al. "The Quantification of Sirolimus by High-Performance Liquid Chromatography-Tandem Mass Spectrometry and Microparticle Enzyme Immunoassay in Renal Transplant Recipients," Clinical Therapeutics, vol. 22, Suppl. B 2000.
Taylor et al. "Simultaneous Quantification of Tacrolimus and Sirolimus, in Human Blood, by High-Performance Liquid Chromatography-Tandem Mass Spectrometry," Therapeutic Drug Monitoring vol. 22, No. 5, p. 608-12, 2000.
Trenerry et al. "The Determination of Vitamin D3 in Bovine Milk by Liquid Chromatography Mass Spectometry," Food Chemistry, Oct. 2010, vol. 125, No. 4, p. 1314-1319.
Vogeser et al. "Candidate Reference Method for the Quanification of Circulating 25-Hydroxyvitamin D3 by Liquid Chromatography-Tandem Mass Spectrometry," Clinical Chemistry, Aug. 2004, vol. 50, No. 8, p. 1415-1417.
Ying et al. "Identification and Structural Elucidation of Vitamin D3 Metabolites in Human Urine Using LC-MS-MS" Chromatographia: An International Journal for Rapid Communication in Chromatography, Electrophoresis and Associated Techniques, Nov. 2008, vol. 69, No. 1-2, p. 103-109.
Zimmer et al. "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, 854:23-35.
U.S. Appl. No. 13/881,848, Jan. 29, 2016, Office Action.
U.S. Appl. No. 13/881,848, Dec. 2, 2016, Notice of Allowance.

* cited by examiner

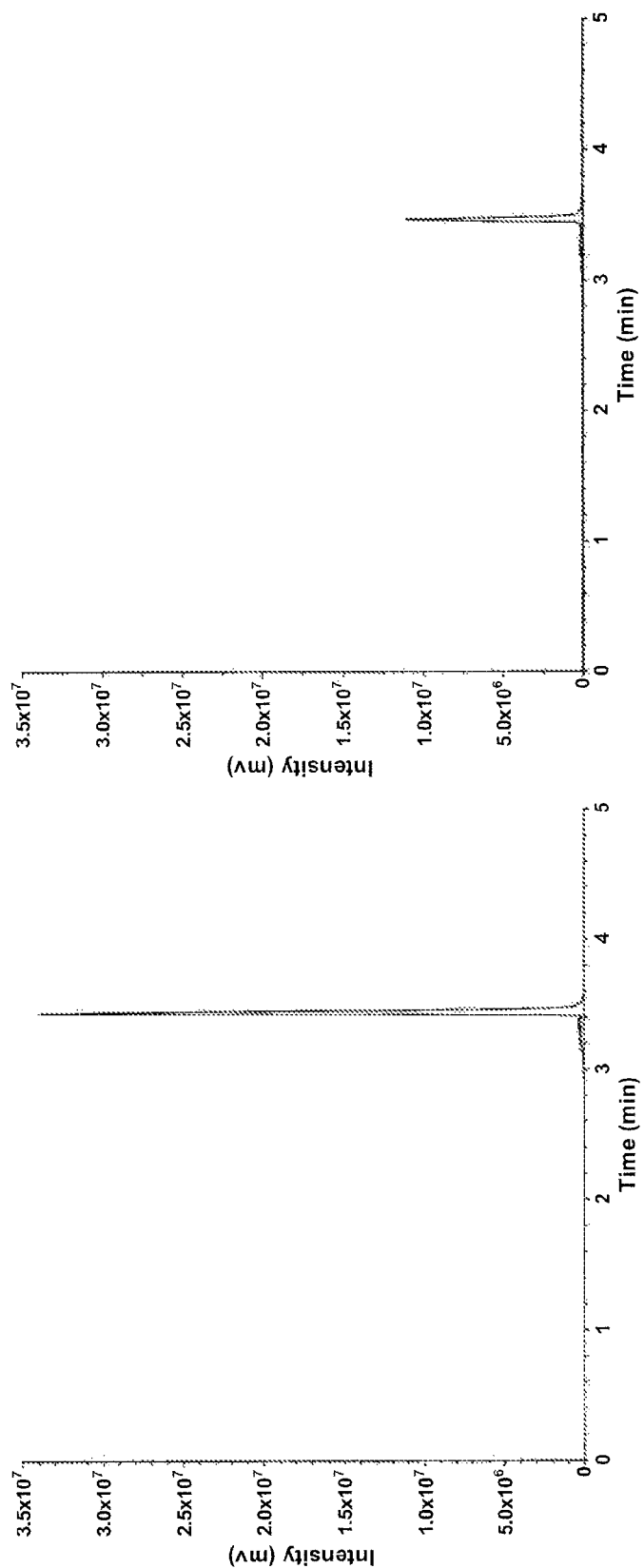

LC-MS CONFIGURATION FOR PURIFICATION AND DETECTION OF ANALYTES HAVING A BROAD RANGE OF HYDROPHOBICITES

CROSS-REFERENCE TO RELATED APPLICATIONS

This application is a continuation of, and claims priority to, U.S. patent application Ser. No. 13/881,848, entitled "LC-MS CONFIGURATION FOR PURIFICATION AND DETECTION OF ANALYTES HAVING A BROAD RANGE OF HYDROPHOBICITIES," filed 5 Nov. 2013, now U.S. Pat. No. 9,625,429, which is the National Stage of, and claims the benefit of and priority to PCT Application Serial No. PCT/US2011/058430, entitled "LC-MS CONFIGURATION FOR PURIFICATION AND DETECTION OF ANALYTES HAVING A BROAD RANGE OF HYDROPHOBICITIES," filed 28 Oct. 2011, which claims the benefit of and priority to U.S. Provisional Patent Application Ser. No. 61/408,266, entitled "LC-MS CONFIGURATION FOR PURIFICATION AND DETECTION OF ANALYTES HAVING A BROAD RANGE OF HYDROPHOBICITIES," filed 29 Oct. 2010, the entirety of each of which is incorporated herein by reference. This application also references PCT Application Serial No. PCT/US2011/058423, entitled "LC-MS SEPARATION AND DETECTION OF VITAMIN D METABOLITES," filed 28 Oct. 2011, which claims the benefit of and priority to U.S. Provisional Patent Application Ser. No. 61/408,385 entitled "LC-MS SEPARATION AND DETECTION OF VITAMIN D METABOLITES," filed 29 Oct. 2010, the entirety of each of which is incorporated herein by reference.

BACKGROUND OF THE INVENTION

1. The Field of the Invention

The invention relates to methods, systems, apparatuses, and kits for LC-MS separation and detection of analytes

2. The Relevant Technology

Liquid chromatography-mass spectrometry (LC-MS) is a powerful analyte detection and measurement technique that is quickly becoming the preferred method of detecting small molecule analytes for diagnostic purposes. However, the instrumentation required for LC-MS is technically complex and, as such, is typically not well suited to the average hospital clinical lab or medical lab technologist. By and large, these labs have not adopted LC-MS diagnostics and, instead, generally use alternative diagnostic techniques, including automated immunoassay, or send the samples out to a reference laboratory for analysis. Moreover, even reference laboratories or other types of testing laboratories including, without limitation, those for testing industrial or environmental samples would make broader use of LC-MS if the procedure was simplified and substantially automated.

Current LC-MS methods require careful selection of the appropriate liquid chromatography column and mobile phases for each different analyte of interest, as well as careful calibration of the mass spectrometer to isolate and identify the analyte of interest. In order to analyze a second different analyte on the same instrument, one or more of the column, the mobile phases, or the mass spectrometer settings generally must be changed and optimized by the LC-MS technologist. Because of the time and technical complexity of such changes, random access analysis of individual samples is costly and inefficient. So instead, samples flagged for analysis for the same or similar analytes are generally grouped into large batches and run together. While this arrangement may reduce the number of changes to the LC-MS system set-up from run-to-run, it significantly increases the time to result for each sample. The high complexity of the LC-MS setup and process calls for having an expert LC-MS technologist on hand all the time to make adjustments, manual changes, and hardware re-configurations to the system.

Since hospitals are typically not equipped or staffed to perform such sophisticated analytical chemistry experiments, LC-MS systems are generally not available at hospitals today. Instead, samples flagged for LC-MS analysis are sent out to a few central reference labs where samples are batched according to the ordered assay type(s). This practice is time-consuming and expensive. In addition, this situation makes it difficult for multiple analyses to be performed on the same sample. As a result, samples may be held for several hours or even days before their batch is analyzed and samples containing multiple analytes of interest may have to be aliquoted separately or placed back into the queue batch each time a different analyte is to be assayed. If the hospital is not near a major reference lab having LC-MS equipment, one must transport the sample to and from the lab, creating a further delay of possibly days. For time sensitive analyses (e.g., for emergency department patients or for samples containing unstable analytes), such delays are unacceptable. For more routine tests, such delays and added expense render many powerful LC-MS diagnostic tests simply unavailable today to many hospitals and diagnostic laboratories.

Efforts have been made to simplify LC-MS analysis by reducing the numbers of different columns and mobile phase buffers needed to purify and analyze a wide range of compounds having different characteristics. For example, Herman reported (*Rapid Commun. Mass Spectrom.* 16: 421-426, 2002) an LC-MS method to analyze a library of drug compounds for the purpose of drug-screening assays, not for diagnostic purposes, using one set of columns, one set of mobile phase buffers, and one set of liquid chromatography conditions (e.g., flow rate, isocratic elution, etc). The method of Herman is applicable to compounds having hydrophobicities spanning about 4 log partition coefficient (log P) units wherein detection within established clinical reference ranges and/or conformity to clinical standards are not required. However, the method of Herman is not applicable to extremely hydrophilic compounds (i.e., log P less than about 1) or to extremely hydrophobic compounds (i.e., log P greater than about 5).

BRIEF SUMMARY

The present invention relates to methods, systems, apparatuses, and kits for purification and detection of analytes having a broad range of hydrophobicities by liquid chromatography-mass spectrometry (LC-MS). Using one set of liquid chromatography columns, one set of mobile phase buffers, and, optionally, a single ionization method (e.g., electrospray ionization), a wide range of analytes can be purified and analyzed on a liquid chromatography-mass spectrometry (LC-MS) system. LC-MS purification and analysis of analytes having a broad range of hydrophobicities is accomplished by selecting LC run parameters (e.g., flow rate, ratios of one buffer to another, temperature, and the like) and MS system parameters (e.g., ionization voltage, desolvation temperature, and the like) that are particular to different analytes without having to make column or buffer changes or any other hardware configuration changes to the LC-MS system. The methods, systems, apparatuses, and kits described herein provide for substantially reduced time to results when multiple samples are analyzed in no particular order. The methods, systems, apparatuses, and kits described herein also provide order and ease of use for a wide range analytes with essentially no compromise in specificity for individual analytes relative to previously described methods.

In one embodiment, a method for detecting and/or quantifying at least two analytes with widely different hydrophobicities using liquid chromatography-mass spectrometry (LC-MS) is disclosed. The method includes (1) providing two or more analytes selected from a first group and a second group, wherein the log partition coefficients (log P) of the two or more analytes selected from the first group and the second group are separated by at least about 4.5 log P units, (2) purifying at least one analyte from each of the first and second groups using a single analytical liquid chromatography column of a liquid chromatography system, one aqueous mobile phase buffer solution of the liquid chromatography system, and one substantially non-aqueous mobile phase buffer solution of the liquid chromatography system, and (3) analyzing the analytes from the first and second groups using a mass spectrometer. In one embodiment, the mass spectrometer may be in fluid communication with the liquid chromatography system. In another embodiment, the mass spectrometer may be "offline" relative to the liquid chromatography system.

The analytes can be contained in the same sample or they can be contained in different samples. Likewise, the analytes can be purified and analyzed in a single LC-MS run or they can be analyzed at different times.

No changes to the LC-MS system hardware are necessary in order to serially purify and analyze analytes separated by about 4.5 or more log P units. That is, it is not necessary to change hardware parameters like columns and mobile phase buffers in order to purify and analyze different analytes. Instead, LC-MS system parameters such as, but not limited to, mobile phase buffer flow rate, a ratio of an aqueous mobile phase buffer solution to a non-aqueous mobile phase buffer solution, a gradient varying ratios of the aqueous and non-aqueous mobile phase buffer solutions, ionization voltage, desolvation temperature, electrode voltage, collision gas temperature, collision gas pressure, collision energy, and combinations thereof can be changed depending on the analyte.

In another embodiment, a method for detecting and/or quantifying two or more analytes with widely different hydrophobicities using LC-MS is disclosed. The method includes (1) providing a single analytical liquid chromatography column of a liquid chromatography-mass spectrometry (LC-MS) system, one aqueous mobile phase buffer solution of the LC-MS system, and one substantially non-aqueous mobile phase buffer solution of the LC-MS, wherein the LC-MS system is configured for purifying and analyzing a plurality of analytes having a log partition coefficients (log P) spanning a range of about −1.2 to about 6 by varying at least one LC-MS system parameter, (2) selecting at least two analytes that span the log partition coefficient range from about −1.2 to about 6; (3) selecting at least one analysis protocol based on the selected analytes, wherein selecting the at least one analysis protocol includes varying at least one LC-MS system parameter, and (4) purifying and analyzing the selected analytes using the LC-MS and the selected analysis protocols, such that a diagnostic quality standard is satisfied for each of the two analytes.

In yet another embodiment, a method is disclosed. The method includes (1) providing a first analyte and a second analyte selected from the group consisting of vitamin D, steroid hormones, protein hormones, proteins, peptides, immunosuppressants, chemotherapeutics, tricyclic antidepressants, azole antifungals, anti-epileptics, anti-retrovirals, opiates and/or opioids, drugs of abuse, barbiturates, benzodiazepines, or a metabolite thereof, wherein the log partition coefficients (log P) of the first and second analytes are separated at least about 4.5 log P units. The method further includes (2) purifying the first analyte and the second analyte using a single analytical liquid chromatography column of a liquid chromatography system, one aqueous mobile phase buffer solution of the liquid chromatography system, and one substantially non-aqueous mobile phase buffer solution of the liquid chromatography system, and (3) analyzing the first analyte and the second analyte using a mass spectrometer that is in fluid communication with the liquid chromatography system.

In still yet another embodiment, a method for detecting and/or quantifying three or more analytes with widely different hydrophobicities using LC-MS is disclosed. The method includes (1) providing a first analyte, a second analyte, and a third analyte, wherein the first analyte has a log partition coefficient (log P) in a range of about −1.2 to about 0, the second analyte has a log P in a range from about 0 to about 5, and the third analyte has a log P greater than about 5 and less than or equal to about 6. In total, this represents the almost the entire practical range of log Ps with the first analyte being very hydrophilic and the third analyte being very hydrophobic and the second analyte being essentially anywhere in between.

The method further includes (2) providing a single analytical liquid chromatography column of a liquid chromatography-mass spectrometry (LC-MS) system, one aqueous mobile phase buffer solution of the LC-MS system, and one substantially non-aqueous mobile phase buffer solution of the LC-MS, and a mass spectrometer, and (3) purifying and analyzing the first, second, and third analytes on the LC-MS system. One will appreciate that the first, second, and third analytes can be analyzed in essentially any order.

In still yet another embodiment, a system for purifying and analyzing analytes of interest by LC-MS is disclosed. The system includes a single analytical liquid chromatography column of a liquid chromatography system, one aqueous mobile phase buffer solution of the liquid chromatography system, and one substantially non-aqueous mobile phase buffer solution of the liquid chromatography system, and a mass spectrometer capable of ionizing, fragmenting, and detecting one or more parent ions or product ions specific to each analyte purified and eluted from the liquid chromatography system.

The liquid chromatography system is capable of effecting purification and elution of each of vitamin D, steroid hormones, protein hormones, proteins, peptides, immunosuppressants, chemotherapeutics, tricyclic antidepressants, azole antifungals, anti-epileptics, anti-retrovirals, opiates and/or opioids, drugs of abuse, barbiturates, benzodiazepines, metabolites thereof, and combinations thereof with the single analytical liquid chromatography column, the one aqueous mobile phase buffer solution, and the one substantially non-aqueous mobile phase buffer solution.

In still yet another embodiment, a kit for purifying and analyzing analytes of interest by LC-MS is disclosed. The kit includes at least one analytical liquid chromatography column, reagents for purifying a plurality of analytes using a liquid chromatography system, wherein the reagents comprise at least one aqueous mobile phase buffer solution and at least one substantially non-aqueous mobile phase buffer solution, and a protocol for analyzing the plurality of analytes using a mass spectrometer. The protocol includes instructions for purifying and analyzing analytes having partition coefficients (log P) ranging from about −1.2 to about 6 using a single analytical liquid chromatography column, a single aqueous mobile phase buffer, and a single substantially non-aqueous mobile phase buffer. In one embodiment, the protocol further includes instructions for purifying and analyzing the analytes having log Ps ranging from about −1.2 to about 6 such that a diagnostic quality standard is satisfied for each analyte in the log P range from about −1.2 to about 6.

In still yet another embodiment, an apparatus for purifying and analyzing analytes of interest having a broad range of hydrophobicities is disclosed. The apparatus includes a single analytical liquid chromatography column of a liquid chromatography system, one aqueous mobile phase buffer solution of the liquid chromatography system, and one substantially non-aqueous mobile phase buffer solution of the liquid chromatography system, wherein the liquid chromatography system is capable of effecting purification and elution of analytes spanning a log partition coefficient (log P) range of about −1.2 to about 6 using the single analytical liquid chromatography column, the one aqueous mobile phase buffer solution, and the one substantially non-aqueous mobile phase buffer solution.

The apparatus further includes a mass spectrometer capable of ionizing, fragmenting, and detecting one or more parent ions or product ions specific to each analyte purified and eluted from the liquid chromatography system, a sample handling device configured to manage a plurality of samples, and a control system linked to each of the liquid chromatography system and the mass spectrometer and configured to control or vary at least one LC-MS system parameter (i.e., a software controlled parameter and not a hardware parameter).

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 5A depicts the selected reaction monitoring ("SRM") signal from 25-OH $D_2$ using ESI to produce the [M+H]+ molecular ion;

FIG. 5B depicts the SRM signal from 25-OH $D_2$ using APCI to produce the [M+H—$H_2O$]+ water loss ion;

DETAILED DESCRIPTION

I. Introduction and Definitions

Figure 1:
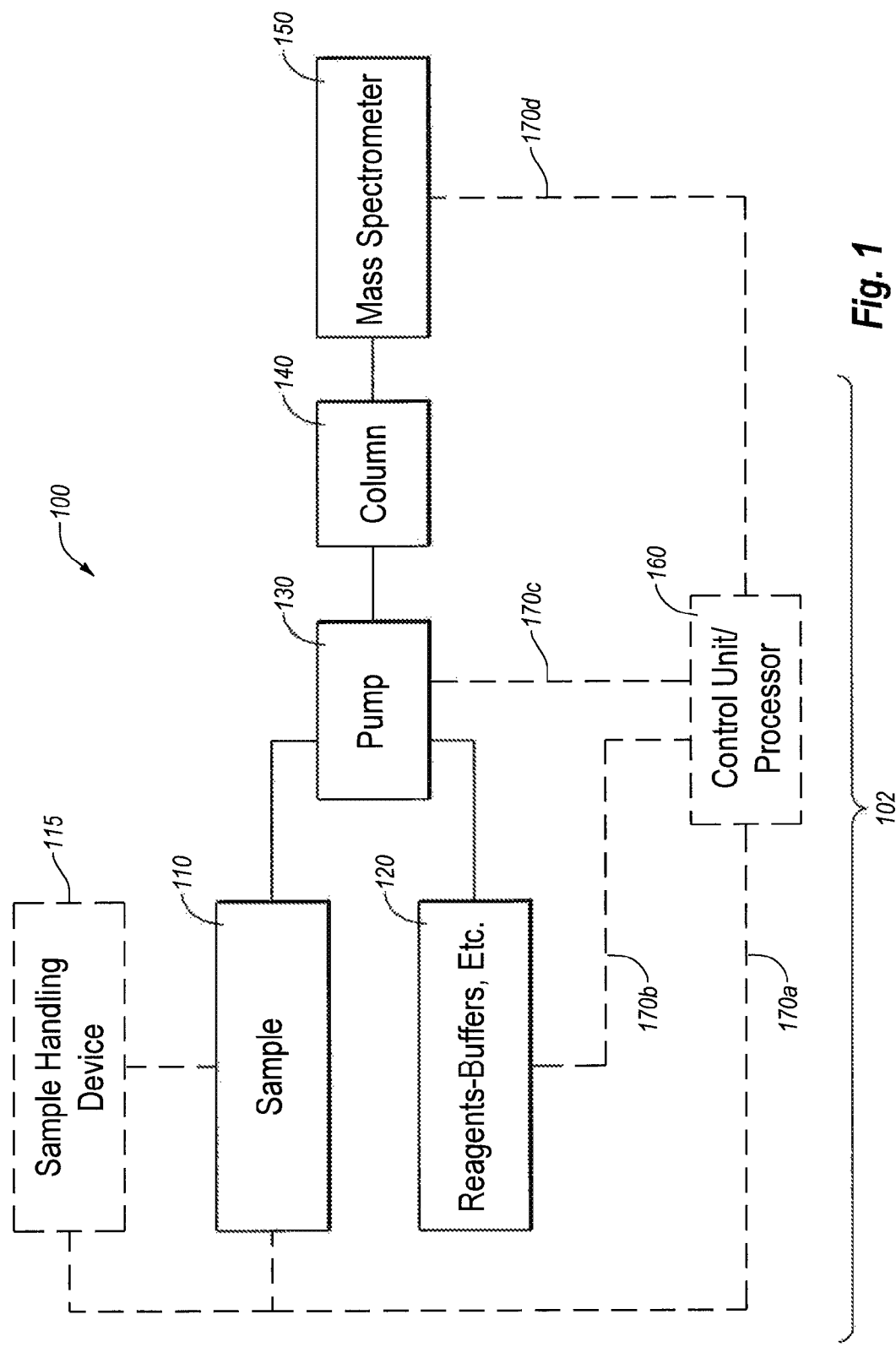
FIG. 1 is a block diagram schematically illustrating a system for purifying and analyzing analytes having a broad range of partition coefficients.

The present invention relates to methods, systems, and kits for purification and detection of analytes having a broad range of hydrophobicities by liquid chromatography-mass spectrometry (LC-MS). Using a single liquid chromatography column (e.g., a single analytical liquid chromatography column) or a single set of liquid chromatography columns (e.g., a single sample clean-up liquid chromatography column in fluid communication with and upstream of the single analytical liquid chromatography column), one set of mobile phase buffers, and, optionally, a single ionization method (e.g., electrospray ionization ("ESI"), atmospheric pressure chemical ionization ("APCI") and other ionization methods as known in the art), a wide range of analytes can be purified and analyzed on a liquid chromatography-mass spectrometry (LC-MS) system. LC-MS purification and analysis of analytes having a broad range of hydrophobicities is accomplished by selecting LC run parameters (e.g., flow rate, ratios of one buffer to another, temperature, and the like) and MS system parameters (e.g., ionization voltage, desolvation temperature, and the like) that are particular to different analytes without having to make column or buffer changes or any other hardware configuration changes to the LC-MS system. Due to the fact that columns, buffers, and the like do not need to be changed between runs with different analyte types, the methods, systems, and kits described herein provide for substantially increased speed and ease of use for a wide range analytes with essentially no compromise in specificity for individual analytes relative to previously described methods.

As used herein, the terms "partition coefficient" and "log P" refer the ratio of concentrations of a compound between two immiscible solvents (e.g., octanol and water) at equilibrium. Hence, to a first approximation, Log P is a measure of how hydrophilic ("water loving") or hydrophobic ("water fearing") a chemical substance is. It should be noted that log P is an exponential function, thus, in general, a change of one unit represents a factor of 10 difference in hydrophobicity.

Purifying and analyzing analytes having a broad range of hydrophobicities, which are estimated by log P measurements, poses particular challenges with current LC-MS technology. This is due in large part to challenges associated with achieving chromatographic separation of such broad ranging compounds. Typically, LC-MS systems separate compounds for analysis in the mass spectrometer using a high-performance liquid chromatography (HPLC) system, which separates compounds based on their hydrophobicity by taking advantage of changes in the partitioning between the stationary and mobile phases. Large differences in hydrophobicity tend to result in vastly different retention characteristics on HPLC.

Generally, a result of this is that changes in the mobile phase (i.e., liquid buffer solutions), stationary phase (column selection), or both are needed to achieve the desired chromatographic separation when working with compounds from different chemical classes (e.g., different and broad ranging log Ps). That is, liquid chromatography hardware (e.g., columns), consumables (e.g., mobile phase buffers), MS set up (e.g., ionization type), and systems parameters (e.g., flow rate, gradients, etc.) are generally optimized to each different analyte type or class of analyte, where classes are defined by a fairly narrow range of log Ps within each given class.

As a consequence, samples to be analyzed are currently grouped together according to the characteristics of the analyte(s) of interest and similar samples are run together in batches on an instrument equipped with a particular set of columns, buffers, and run parameters that are unique to the analyte of interest. In order to run samples containing a second, different analyte of interest, one or more of the column, the mobile phase buffers, or the run parameters generally must generally be changed and optimized by the LC-MS operator. While this arrangement may reduce the number of changes to the LC-MS system set-up from run-to-run, it significantly increases the time to result for each sample. In addition, this situation makes it difficult for multiple analyses to be performed on the same sample. As a result, samples may have to wait several hours or even days before their batch is analyzed and samples containing multiple analytes of interest have to be divided into separate aliquots or placed back into the queue each time a different analyte is to be assayed. For time sensitive analyses (e.g., for emergency department patients or for samples containing unstable analytes), such delays are unacceptable.

The present invention seeks to simplify LC-MS purification and analysis of analytes from multiple and broad ranging chemical classes (e.g., a broad range of log partition coefficients) by presenting methods, systems, apparatuses, and kits that are configured for assaying (i.e., purifying and analyzing) compounds having a broad range of hydrophobicities using a single set of liquid chromatography columns (e.g., a clean-up column and an analytical column) and a single set of mobile phase buffers (e.g., an aqueous buffer and a non-aqueous buffer). And instead of changing columns and buffers when switching from one chemical class to another, LC-MS purification and analysis is accomplished by selecting LC run parameters (e.g., flow rate, ratios of one buffer to another, temperature, and the like) and MS system parameters (e.g., ionization voltage, desolvation temperature, and the like) that are particular to each different analytes or classes of analytes.

The difficulty in developing a unified LC-MS method that can be used to purify and assay compounds having a broad range of log Ps by LC-MS can be illustrated by reference to Table 1 (below).

TABLE 1

|  | logP |
|---|---|
| Endocrinology | |
| Vitamin D | |
| 25OH vitamin $D_2$ | 5.69 |
| 25OH vitamin $D_3$ | 5.61 |
| Steroids | |
| Testosterone | 4.44 |
| Cortisol (hydrocortisone) | 1.26 |
| Cortisone | 1.58 |
| Progesterone | 3.58 |
| Hydroxyprogesterone | 3.52 |
| Prednisone | 2.07 |
| Androstenedione | 2.93 |

TABLE 1-continued

| | logP |
|---|---|
| Therapeutic Drug Monitoring | |
| Immunosuppressants | |
| Tacrolimus | 3.3 |
| Everolimus | 5.01 |
| Sirolimus | 4.3 |
| Cyclosporin A | 4.12 |
| Chemotherapeutics | |
| Methotrexate | 0.94 |
| Busulfan | −1.15 |
| 5-Fluorouracil | −0.9 |
| Docetaxel | 2.4 |
| Pain management & Drugs of Abuse | |
| NIDA 5 | |
| Phencyclidine | 4.14 |
| Benzoylecgonine | 1.64 |
| Cocaine | 1.91 |
| Delta9-THC | 5.53 |
| 11-norDelta-9-THC-COOH | 4.6 |
| Amphetamines | |
| Amphetamine | 1.7 |
| Methamphetamine | 2.2 |
| MDMA | 1.98 |
| MDEA | 2.31 |
| MDA | 1.46 |
| Opiates/Opioids | |
| Hydromorphone | 1 |
| Norhydrocodone | 0.89 |
| Norcodeine | 1.07 |
| Morphine | 1.73 |
| Hydrocodone | 1.27 |
| Codeine | 1.45 |
| Noroxycodone | 0.1 |
| Oxymorphone | 0.21 |
| Dihydrocodeine | 1.63 |
| Oxycodone | 0.48 |
| 6-MAM | 1.81 |
| Tapentadol | 3.43 |
| Norfentanyl | 3.94 |
| Fentanyl | 4.59 |
| Tramadol | 2.53 |
| Methadone | 4.55 |
| Metoprolol | 2.18 |

The compounds listed in Table 1 can be analyzed by LC-MS for a variety of clinical and drug monitoring purposes. Under current practice, however, LC-MS analysis relies on using protocols that are particular to the different classes of analytes. The compounds listed in Table 1 have log Ps ranging from about −1.2 (busulfan) to about 6 (25OH vitamin $D_2$), which represents a difference in hydrophobicity over slightly more than about seven orders of magnitude. This is a very broad range of hydrophobicities and it is surprising and unexpected that such a broad range of analytes can be purified and analyzed by LC-MS using one set of liquid chromatography columns, one set of mobile phase buffers, and, optionally, a single ionization method.

As used herein, the term "purification" does not refer to removing all materials from the sample other than the analyte(s) of interest. Instead, in one aspect, purification may refer to a procedure that enriches the amount of one or more analytes of interest relative to one or more other components of the sample. In another aspect, purification can be used to remove one or more interfering substances, e.g., one or more substances that would interfere with detection of an analyte ion by mass spectrometry.

As used herein, "sample" refers to any fluid or liquid sample, including extractions of solid materials or swabs from environmental surfaces and "biological sample" refers to any sample from a biological source such as, but not limited to, hair, bodily tissue (e.g., skin or tissue biopsy), blood, plasma, deproteinated plasma, serum, deproteinated serum, sputum, bile, saliva, urine, feces, tears, perspiration, swabs from body sites, suspensions of microorganisms, and the like.

As used herein, "kit" refers to two or more components comprising reagents, devices, calibrators, controls, standards, or any combination thereof, for performance of a common method, regardless of whether the two or more components are provided within a single package or multiple packages.

As used herein, "chromatography" refers to a process in which a chemical mixture carried by a liquid, gas or supercritical fluid is separated into components as a result of differential distribution of the solutes as they flow around or over a stationary phase or chemically interact with a liquid or solid phase.

As used herein, "liquid chromatography" (LC) means a process of selective retention of one or more components of a fluid solution as the fluid uniformly percolates through a column of a finely divided substance, or through capillary passageways. The retention results from the distribution of the components of the mixture between one or more stationary phases and the bulk fluid, (i.e., mobile phase), as this fluid moves relative to the stationary phase(s). "Liquid chromatography" includes, without limitation, reverse phase liquid chromatography (RPLC), high performance liquid chromatography (HPLC), ultra high performance liquid chromatography (UHPLC), supercritical fluid chromatography (SFC) and ion chromatography.

As used herein, the term "HPLC" or "high performance liquid chromatography" refers to liquid chromatography in which the degree of separation is increased by forcing the mobile phase under pressure through a stationary phase, typically a densely packed column.

As used herein, the term "UHPLC" or "ultra high performance liquid chromatography" refers to a liquid chromatography technique similar to HPLC except the operating pressures are higher than HPLC (e.g., about 100 MPa vs. about 40 MPa), the columns are typically smaller in diameter, the particles of packing material are generally smaller, and resolution can be greater.

As used herein, "mass spectrometry" (MS) refers to an analytical technique to filter, detect, identify and/or measure compounds by their mass to charge ratio, of "Dale" (also commonly denoted by the symbol "m/z"). MS technology generally includes (1) ionizing the compounds and potentially fragmenting the compounds; and (2) detecting the molecular weight of the charged compound and/or fragment ion and calculating a mass-to-charge ratio (Dale). The compound may be ionized and detected by any suitable means. A "mass spectrometer" generally includes an ionizer and an ion detector.

The term "ESI" or "electrospray ionization" refers to a technique used in mass spectrometry to produce ions. It is especially useful in producing ions from macromolecules because it overcomes the propensity of these molecules to fragment when ionized. In ESI a stream of fluid is ejected from a nozzle, cone or other directive device which may or may not be electrically charged. Molecular ions (e.g., [M+H]+) may be formed in the liquid phase or as a function of the physic-chemical processes occurring during evaporation of the solvent shell around the analyte or in the gas phase.

The term "ionization" as used herein refers to the process of generating an analyte ion having a net electrical charge. Negative ions are those having a net negative charge, while positive ions are those having a net positive charge.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

The term "about" as used herein in reference to quantitative measurements, refers to the indicated value plus or minus 10%.

II. Systems and Apparatuses for LC-MS Purification and Detection of Analytes Having a Broad Range of Hydrophobicities Referring now to FIG. 1, a system 100 for LC-MS purification and detection of analytes from a broad range of chemical classes is schematically illustrated. The system 100 includes a liquid chromatography system 102 capable of effecting purification of analytes from a broad range of chemical classes and a mass spectrometer 150 capable of ionizing, fragmenting, and detecting one or more precursor ions or product ions specific to each analyte of interest.

The liquid chromatography system 102 schematically illustrated in FIG. 1 includes a sample 110, reagents 120 for purifying a wide variety of analytes of interest from the sample 110 by liquid chromatography, a liquid chromatography column 140 capable of effecting separation of analytes having a broad range of hydrophobicities, and a fluid handling pump 130 in fluid communication with the sample 110, reagents 120, and the liquid chromatography column 140. The liquid chromatography column 140 can include a single liquid chromatography column (e.g., a single analytical liquid chromatography column) or a single set of liquid chromatography columns (e.g., a single sample clean-up liquid chromatography column in fluid communication with and upstream of the single analytical liquid chromatography column).

In one embodiment, the reagents 120 include a single liquid chromatography buffer. In another embodiment, the reagents 120 may include a single substantially aqueous buffer, a single substantially non-aqueous buffer, and at least one wash buffer. In one embodiment, the single substantially aqueous buffer and the single substantially non-aqueous buffer may include a source of ammonium ions (e.g., ammonium formate or ammonium acetate). The reagents 120 may also include one or more reagents for sample preparation, such as a protein precipitation reagent selected for removing proteins that may interfere with assaying an analyte of interest.

As illustrated in FIG. 1, the system 100 further includes an optional control unit 160 that can be linked various components of the system 100 through linkages 170a-170d. For example, the control unit 160 can be linked to the sample 110 to control sample application, the reagents 120 to control the application of various reagents, the pump 130 to control fluid handling, flow rates, etc, and to the mass spectrometer 150 to control mass spectrometry parameters. In the illustrated embodiment, the control unit 160 can also serve as a data processing unit to, for example, process data from the mass spectrometer 150.

In some embodiments, the system 100 is designed to be used by a clinician or a general laboratory technician who is not necessarily expert in all aspects of sample preparation, LC-MS operations, and/or LC-MS methods development. As such, the control unit 160 can be designed to encapsulate the LC/MS data system environment by providing a user with a simplified application interface that can be used to initiate and monitor essentially all aspects of assaying a sample 110 without requiring the user to interact with the overall hardware and control systems of the system 100. The control unit 160 is therefore configured to provide a degree of separation between the user and the underlying services that control devices, data files and algorithms for translating data to a user readable form. That is, the control unit 160 eliminates the need for the user to be aware of or in control of hardware for analyzing clinical samples and provides a simplified interface to send and receive information from the mass spectrometer.

The control unit 160 may be configured to internally monitor each sample analysis request and is capable of tracking the analysis request from start to finish through the system 100. Once data for a sample 110 has been acquired by the system 100, the control unit 160 may be configured to automatically start post processing the data based on the type of assay selected by the user. Moreover, the control unit 160 can be configured to automatically select post processing parameters based on the type of assay selected by the user, further reducing the need for the user to interact with the system once the assay has been selected and started for analysis. The control unit 160 can be designed as a layer that fits between an LC/MS system 100 and the user to reduce the complexity needed to set up sample assays for acquisition. The control system 160 can also be configured to return only the most relevant data to the user to avoid overwhelming the user with extraneous information.

The control unit 160 can be configured to control the flow of information through the system 100. The following list provides an abbreviated overview of information flow through the system 100 in various embodiments:

i. The user submits a sample 110 to the system 100. The system 100 can be set up such that the user then submits an assay request through the control system 160. Alternatively, the control system 160 can be linked to a sample detection device (e.g., a bar code scanner or an RFID scanner) that detects the presence of the sample and the type of analysis ordered and that automatically submits an assay request through the control system 160.
  ii. The control system 160 translates the assay data and submits it to the LC-MS system 100. Among other things, this can be used by the system 100 to set up and initiate the assay parameters (e.g., flow rate, a ratio of the aqueous mobile phase buffer solution to the non-aqueous mobile phase buffer solution, a gradient varying ratios of the aqueous and non-aqueous mobile phase buffer solutions, ionization voltage, desolvation temperature, timing and magnitude of voltages applied to various mass spectrometer electrodes, collision energy, collision gas temperature, collision gas pressure, etc.).
  iii. The control system 160 can monitor the status of the sample collection from the LC/MS system and, once completed, initiate data processing to generate a result specific for the assay type selected by the user.

iv. When the assay and the data analysis are complete, the control system 160 can notify the user that the results are complete for the submitted sample and send the results to the user. The user can then typically display the results for the assayed compound either numerically or graphically.

In one embodiment, the system can further include a sample handling device 115 configured to manage a plurality of samples. The sample handling device 115 can include a carrousel or tray with multiple sample racks. In turn, each sample rack can include one or more sample container positions capable of holding a sample container, e.g., a tube.

In one embodiment, the system 100 can further include a sample detection device (not pictured) operably coupled to or integrated with the sample handling device 115. The sample detection device can work with the sample handling device 115 or independently of the sample handling device 115 perform at least one of the following functions:

i. identify samples entering the system;
ii. identify an analyte of interest in the samples entering the system;
iii. select an assay protocol based on the analyte of interest;
iv. direct the sample handling device and/or the control system to initiate analysis of the analyte of interest in the sample;
v. direct the control system to select one or more reagents based upon the assay protocol selected for the analyte of interest;
vi. direct the control system to select a liquid chromatography mobile phase condition based upon the assay protocol selected for the analyte of interest and cause the liquid chromatography system to purify the analyte of interest;
vii. direct the control system to select a mass spectrometer setting based upon the assay protocol selected for the analyte of interest and cause the mass spectrometer to create mass spectral data associated with the selected analyte of interest; or
viii. direct the control system to analyze the mass spectral data associated with the selected analyte of interest to identify the presence and/or concentration of the analyte of interest.

Additional discussion of an example of an automated LC-MS system can be found in U.S. Provisional Patent Application Ser. No. 61/408,180 entitled "AUTOMATED SYSTEM FOR SAMPLE PREPARATION AND ANALYSIS," filed 29 Oct. 2010 with inventors Robert DeWitte, Juhani Siidorov, Vesa Nuotio, Raimo Salminen, Jarmo Vehkomäki, Jukka Saukkonen, Bill Östman, Joe Senteno, John Edward Brann III, Joseph L. Herman, and Jeffrey A. Zonderman, the entirety of which is incorporated herein by reference.

Suitable samples 110 include any sample that may contain an analyte of interest, such as, but not limited to, biological samples and so-called "neat" samples that contain an analyte or analytes of interest dissolved in a suitable solvent. For example, samples obtained during the manufacture of an analyte can be analyzed to determine the composition and yield of the manufacturing process. Samples from environmental sources include, without limitation, water, toxins, and swabs from environmental surfaces. In certain embodiments, a sample is a biological sample; that is, a sample obtained from any biological source, such as an animal, a cell culture, an organ culture, etc. Particularly preferred are samples obtained from a human, such as a blood, plasma, deproteinated plasma, serum, sputum, muscle, urine, saliva, tear, cerebrospinal fluid, swabs from body sites, suspensions of microorganisms or tissue sample. Such samples may be obtained, for example, from a patient; that is, a living person presenting themselves in a clinical setting for diagnosis, prognosis, or treatment of a disease or condition.

Samples may be processed or purified to obtain preparations that are suitable for the desired type of chromatography and/or for analysis by mass spectrometry. Various procedures may be used for this purpose depending on the type sample or the type of chromatography. Examples include filtration, extraction, precipitation, centrifugation, dilution, combinations thereof and the like. Protein precipitation is one example method of preparing a liquid biological sample, such as serum or plasma, for chromatography. In one embodiment, a volume of the liquid sample is added to a sufficient volume of methanol to cause precipitation of most of the proteins in the sample while the analyte of interest is left in the resulting supernatant. The samples can then be centrifuged to separate the liquid supernatant from the pellet. The resultant supernatants can then be applied to liquid chromatography and mass spectrometry analysis. In some embodiments, the system 100 includes a quality control standard that can be used to track at least one of the handling, separation, ionization, fragmentation, or detection of the analyte(s) of interest. For example, hexadeuterated 25-OH $D_3$ ($d_6$-25-OH $D_3$) may be used as a quality control standard or an internal standard in assays for vitamin D and vitamin D metabolites. Persons having skill in the art can select suitable quality control standards or internal standards for use with the analytes of interest discussed herein.

The sample, or the processed sample, may be purified prior to analysis by mass spectrometry. Such purification, or sample clean-up, refers to a procedure that enriches of one or more analytes of interest relative to one or more other components of the sample. Typically, one or more methods including, without limitation, liquid chromatography, HPLC, UHPLC, precipitation, dialysis, affinity capture, electrophoresis, or other suitable methods known in the art, are used for the purification.

Various methods have been described involving the use of HPLC for sample clean-up prior to mass spectrometry analysis. See, e.g., Taylor et al., Therapeutic Drug Monitoring 22:608-12 (2000) (manual precipitation of blood samples, followed by manual C18 solid phase extraction, injection into an HPLC for chromatography on a C18 analytical column, and MS/MS analysis); and Salm et al., Clin. Therapeutics 22 Supl. B:B71-B85 (2000) (manual precipitation of blood samples, followed by manual C18 solid phase extraction, injection into an HPLC for chromatography on a C18 analytical column, and MS/MS analysis). One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles may include a bonded surface that interacts with the various chemical moieties to facilitate separation of the analytes of interest. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used wherein a test sample may applied to a first column (e.g., a clean-up column such as a Cyclone P column or the like) at the inlet port, eluted with a solvent or solvent mixture onto a second column (e.g., an analytical column such as a Hypersil Gold PFP, Accucore PFP™, Halo or the like), and eluted with a solvent or solvent mixture from the second column to the outlet port. Different solvent modes may be selected for eluting the analytes. For example, liquid chromatography may be performed using a gradient mode, an isocratic mode, or a polytyptic (i.e. mixed) mode.

Recently, high turbulence liquid chromatography ("HTLC"), also called high throughput liquid chromatography, has been applied for sample preparation prior to analysis by mass spectrometry. See, e.g., Zimmer et al., J. Chromatogr. A 854:23-35 (1999); see also, U.S. Pat. Nos. 5,968,367; 5,919,368; 5,795,469; and 5,772,874, each of which is hereby incorporated by reference in its entirety. Traditional HPLC analysis relies on column packings in which laminar flow of the sample through the column is the basis for separation of the analyte of interest from the test sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the analyte(s) of interest. In such embodiments samples may be extracted using an HTLC extraction cartridge which captures the analyte, then eluted and chromatographed on an HPLC or other column prior to ionization. Because the steps involved in these two column purification steps can be linked in an automated fashion, the requirement for operator involvement during the purification of the analyte can be minimized.

The terms "mass spectrometry" or "MS" as used herein refer to methods of filtering, detecting, and measuring ions based on their mass-to-charge ratio, or "Da/e." In general, one or more molecules of interest, such a vitamin D metabolites, are ionized and the ions are subsequently introduced into a mass spectrographic instrument where, due to a combination of magnetic and electric fields, the ions follow a path in space that is dependent upon mass ("m" or "Da") and charge ("z" or "e").

The mass spectrometer 150 will include an ion source for ionizing the fractionated sample and creating charged molecules for further analysis. For example ionization of the sample may be performed by electrospray ionization (ESI). Other ionization techniques include, but are not limited to, atmospheric pressure chemical ionization (ACPI), photoinonization, electron impact ionization, chemical ionization, fast atom bombardment (FAB)/liquid secondary ion mass spectrometry (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., Da/e). Suitable analyzers for determining mass-to-charge ratios include quadrupole analyzers, ion traps analyzers, Fourier transform ion cyclotron resonance (FTICR) mass analyzers, electrostatic trap analyzers, magnetic sector analyzers and time-of-flight analyzers. The ions may be detected by using several detection modes. For example, selected ions may be detected (i.e., using a selective ion monitoring mode (SIM)), or alternatively, ions may be detected using selected reaction monitoring (SRM) or multiple reaction monitoring (MRM) (MRM and SRM are essentially the same experiment.). Ions can also be detected by scanning the mass spectrometers to detect all the precursor ions simultaneously or all the products ions of a specific precursor ion simultaneously or both.

In one embodiment, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and Da/e. The voltage and amplitude can be selected so that only ions having a particular Da/e travel the length of the quadrupole, while all other ions are deflected. Thus, quadrupole instruments can act as a "mass filter," a "mass separator" or an ion lens for the ions injected into the instrument.

One can often enhance the resolution of the MS technique by employing "tandem mass spectrometry" or "MS/MS" for example via use of a triple quadrupole mass spectrometer. In this technique, a first, or parent, or precursor, ion generated from a molecule of interest can be filtered in an MS instrument, and these precursor ions subsequently fragmented to yield one or more second, or product, or fragment, ions that are then analyzed in a second MS procedure. By careful selection of precursor ions, only ions produced by certain analytes are passed to the fragmentation chamber (e.g., a collision cell), where collision with atoms of an inert gas to produce these product ions. Because both the precursor and product ions are produced in a reproducible fashion under a given set of ionization/fragmentation conditions, the MS/MS technique can provide an extremely powerful analytical tool. For example, the combination of ion selection or filtration and subsequent fragmentation can be used to eliminate interfering substances, and can be particularly useful in complex samples, such as biological samples.

For example, a flow of liquid solvent from a chromatographic column, possibly containing one or more analytes of interest, enters the heated nebulizer interface of a LC-MS/MS analyzer and the solvent/analyte mixture is converted to vapor in the heated tubing of the interface. Ions derived from the analytes of interest may be formed in the liquid phase and subsequently ejected into the gas phase by nebulization in the ESI source or by reactions between neutral analytes and reactive ions (e.g., ammonium ions) as the analytes enter the gas phase.

The ions pass through the orifice of the instrument and enter the first quadrupole. Quadrupoles 1 and 3 (Q1 and Q3) are mass filters, allowing selection of ions based on their mass to charge ratio (Da/e). Quadrupole 2 (Q2) is the collision cell, where ions are fragmented. The first quadrupole of the mass spectrometer (Q1) selects for molecules with the mass to charge ratios ("Da/e") of ions specific to each analyte of interest to be analyzed. Ions with the correct Da/e ratios of the selected analyte of interest are allowed to pass into the collision cell (Q2), while unwanted ions with any other Da/e are ejected from or collide with the sides of the quadrupole (Q1) and are eliminated. Ions entering Q2 collide with neutral gas molecules (e.g., argon) and fragment. This process is called Collision Activated Dissociation (CAD). The fragment ions generated are passed into quadrupole 3 (Q3), where the fragment ions of the chosen analyte of interest are selected while other ions are eliminated. As ions collide with the detector they produce a pulse of electrons that are converted to a digital signal.

Mass spectrometry instruments can vary slightly in determining the mass of a given analyte. Thus, the term "about" in the context of mass of an ion or the Dale of an ion refers to +/−0.2, +/−0.3, or +/−0.5 atomic mass units or Daltons (Da).

The acquired data is relayed to a computer, which plots voltage versus time. The resulting mass chromatograms are similar to chromatograms generated in traditional HPLC methods. Concentrations of the analytes of interest may be determined by calculating the area under the peaks in the chromatogram. The concentration of the analyte or analytes of interest in the sample is typically determined either by comparing the area under the peaks to a calibration curve or comparing the ratio of internal standards (e.g., deuterated 25-hydroxyvitamin $D_3$) to test samples.

III. Kits for LC-MS Purification and Detection of Analytes from a Broad Range of Chemical Classes In one embodiment, a kit for performing LC-MS of a sample containing at least one analyte of interest is disclosed. The kit includes reagents for purifying, eluting and analyzing a plurality of analytes of interest using an LC-MS system, and a protocol that includes instructions for purifying and analyzing the plurality of analytes of interest having partition coefficients (log P) ranging from about −1 to about 6 using the LC-MS system.

Suitable examples of analytes of interest that can be purified, eluted and analyzed using the methods systems and kits described herein include, but are not limited to, vitamin D, steroid hormones, immunosuppressants, chemotherapeutics, tricyclic antidepressants, azole antifungals, anti-epileptics, anti-retrovirals, opiates and/or opioids, drugs of abuse, barbiturates, benzodiazepines, metabolites thereof, and combinations thereof.

In one embodiment, the protocol may include instructions relating to sample handling and preparation, liquid chromatography conditions (e.g., flow rates, gradients, columns, temperature, etc.), composition of buffers for LC-MS, mass spectrometer settings (e.g., spray voltage, desolvation temperature, sheath gas pressure, voltage and scan settings for the mass analyzer(s), etc.).

The protocol included in the kit can also include instructions for purifying and analyzing the analytes having log Ps ranging from about −1.2 to about 6 such that a diagnostic quality standard is satisfied for each analyte in the log P range from about −1.2 to about 6.

As used herein, the term "diagnostic quality standard" refers to an analytical performance aspect that includes achieving reproducible quantitation for each analyte within specified detection limits, with specified precision and substantially no carry-over from sample to sample.

As used herein, "detection limit(s)" refers to a limit that at least spans the reference range for a given analyte, the lower limit of quantitation being no higher than the low end of the reference range and the upper limit of quantitation being no lower than the upper end of the reference range, wherein the reference range is relevant to a particular application including, without limitation, clinical, industrial and environment applications.

Lower and upper clinical reference ranges for many of the compounds discussed herein are listed in Table 2 (below) in the "Low" and "High" columns, respectively. Additional examples of lower and upper reference ranges for most clinically relevant analytes of interest can be found in *Tietz Textbook of Clinical Chemistry and Molecular Diagnostics* (Burtis et al, Saunders; 4th edition (1 Jul. 2005), ISBN: 0721601892), the entirety of which is incorporated herein by reference. Note, however, that Table 2 and Tietz relate to clinical reference standards as they are now recognized in clinical practice; however, detection limits and clinical reference ranges are continuously evolving. Note also, that clinical reference ranges may vary depending on the standard of care in medical practice and or regulatory bodies in different countries (e.g., the United Stated vs. France). Likewise, because different age groups, genders, and ethnic groups are known to respond differently to some drugs, clinical reference ranges can also vary depending on the groups being tested.

Note also that the lower and upper ends of the clinical reference range do not necessarily represent the limit of detection and the limit of quantitation. For example, the limits of detection and quantitation may be as much as several orders of magnitude lower than the lower clinical reference range. Likewise, the upper range of concentration that can be accommodated by the methods and apparatuses described herein may be much higher than the upper clinical reference range.

As used herein, the term "precision" refers to reproducibility of specific measurements as measured by a coefficient of variation for repeat measurements of a single sample. Precision is customarily determined as a step of assay development, wherein coefficients of variation are derived from repeat measurements on the same day, over different days, etc. Precision requirements vary from one analyte to another depending on current medical practice; however it is generally understood that coefficients of variation below 15% are preferred.

As used herein, the term "substantially no carry-over" refers to a situation where essentially no sample contamination from previous analysis remains in the system (i.e., the LC-MS system) between analyses. The extent of carry-over in analytical instruments can be assessed in a number of ways. One method involves running a number of blank samples in order to establish a clear baseline, running a number of samples having a high concentration of an analyte of interest (e.g., 25OH vitamin $D_3$), followed by assaying blank samples again to ensure a return to baseline. Carry-over can also be assessed by serially analyzing low- and high-concentration control samples (e.g., samples representing the lower and upper limits of quantitation). In one example, "carry-over" is no larger than 0.1% of the blank immediately after analyzing a sample having a high concentration of an analyte of interest. In another example, "carry-over" is no larger than 20% of the lower limit of quantitation (LLOQ) after analyzing a sample at the upper limit of quantitation (ULOQ).

In one embodiment, the kit further includes either a single liquid chromatography column (e.g., a single analytical liquid chromatography column) or a single set of liquid chromatography columns (e.g., a single sample clean-up liquid chromatography column that, when in use, is in fluid communication with and upstream of the single analytical liquid chromatography column) capable of effecting separation of a variety of analytes from a biological matrix and/or from a "neat" sample, at least one liquid chromatography buffer solution containing a source of ammonium ions, and at least one quality-control standard or internal standard for tracking at least one of separation, ionization, fragmentation, or detection of at least one analyte of interest.

Chromatographic columns typically include an inlet port for receiving a sample and an outlet port for discharging an effluent that includes the fractionated sample. For example, a test sample may applied to the column at the inlet port, eluted with a solvent or solvent mixture, and discharged at the outlet port. In another example, more than one column may be used wherein a test sample may applied to a first column (e.g., a clean-up column) at the inlet port, eluted with a solvent or solvent mixture onto a second column (e.g., an analytical column), and eluted with a solvent or solvent mixture from the second column to the outlet port.

Many types of HPLC and UHPLC columns are commercially available and can be selected based on various criteria known to persons having ordinary skill in the art. For example, commercially available HPLC and UHPLC columns include normal-phase (polar stationary phases and non-polar mobile phases), reverse-phase (the stationary phase is non-polar and the mobile phase is polar), ion-exchange (charged species on the stationary phase and charged species in the mobile phase), and affinity chromatography (based on specific interactions in a lock-and-key paradigm between analytes and matrix-bound ligands). In one embodiment, the liquid chromatography is reverse-phase. Suitable reverse phase columns include, but are not limited to, C-4, C-8, C-18, Hypersil Gold PFP, Accucore PFP™, Halo and the like.

In one embodiment, the one aqueous mobile phase buffer solution and the one substantially non-aqueous mobile phase buffer solution include a source of ammonium ions. Acceptable examples of ammonium ion sources include ammonium formate and/or ammonium acetate. In one embodiment, ammonium formate and/or ammonium acetate may be included in the mobile phase buffer in an amount ranging from about 2 mM to about 10 mM, or about 4 mM to about 8 mM, or about 10 mM. Lower or higher amounts of ammonium formate and/or ammonium acetate may be used (e.g., about 0.1 mM to about 20 mM, 50 mM, or 100 mM), but below approximately about 2 mM the numbers of ammonium ions in solution and/or the gas phase may be insufficient to promote ionization of the analytes of interest; amounts above approximately about 10 mM increase the risk that charge-charge repulsion of ammonium ions in solution and/or the gas phase can produce artifacts and reduce sensitivity.

Ammonium formate and ammonium acetate are acceptable sources of ammonium ions for use in LC-MS. Ammonium formate's pKa is lower than ammonium acetate's and, as such, the analytes of interest will be expected to be more fully ionized in the buffer solution, which may be desirable in some instances. Both ammonium formate and ammonium acetate are acceptable because they are sources of volatile ions and are not expected to interfere with mass spectrometry results. In contrast, ammonium chloride, which is also a source of ammonium ions, is generally considered to be unacceptable for use in LC-MS because the chloride is not volatile and would therefore be expected to foul the mass spectrometer.

In one embodiment, the one aqueous mobile phase buffer solution includes an aqueous solution (e.g., water, ammonium formate, and formic acid). In one embodiment, the one substantially non-aqueous mobile phase buffer solution includes a non-aqueous solution (e.g., methanol, ammonium formate, and formic acid). Other organic phases that can be used include, but are not limited to, acetonitrile, ethanol, isopropanol, and combinations thereof. Samples containing one or more analytes of interest can be loaded and washed with aqueous buffer and eluted in an aqueous to non-aqueous gradient or isocratically (e.g., with 100% non-aqueous buffer). In one embodiment, the reagents included in the kit can further include a chromatography wash buffer configured to wash the system in between samples. In one example, the wash buffer may include isopropyl alcohol ("IPA"), acetonitrile ("ACN") and acetone. In another embodiment, the wash buffer may be a high pH aqueous wash buffer of about 8.0 to 10 pH. Optionally, the wash buffer may contain a chelating agent such as, but not limited to, EDTA.

Figure 2:
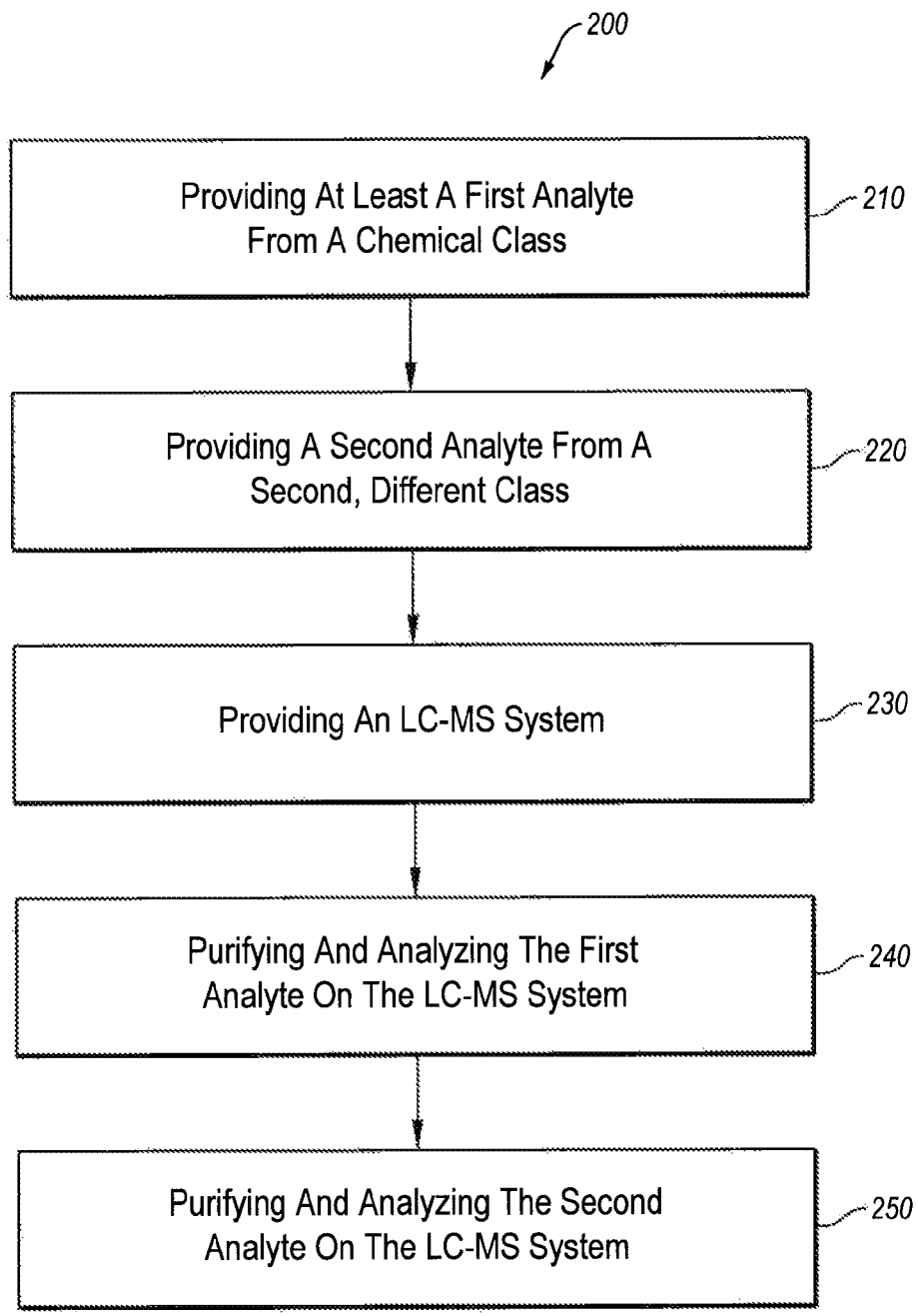
FIG. 2 is a flow diagram illustrating a method for purifying and analyzing analytes having a broad range of partition coefficients by liquid chromatography-mass spectrometry (LC-MS)

IV. Methods for Purifying and Analyzing Analytes Having a Wide Range of Hydrophobicities Referring now to FIG. 2, a method 200 for purifying and analyzing analytes having a wide range of hydrophobicities using liquid chromatography-mass spectrometry (LC-MS) is illustrated. The illustrated method 200 includes an action 210 of providing at least a first analyte from a first chemical class and an action 220 of providing at least a second analyte of interest from a second chemical class that is different from the first chemical class. The first and second analytes of interest have log partition coefficients (log P) spanning a range from about −1.2 to about 6. The method further includes an action 230 of providing an LC-MS system that includes a single analytical column configured to at least partially purify each of the first and second analytes of interest, a mass spectrometer (MS), a single aqueous mobile phase buffer solution, and a single substantially non-aqueous mobile phase buffer solution. In one embodiment, the mobile phase buffer solutions each contain a source of ammonium ions. The method further includes an action 240 of purifying and eluting the first analyte of interest for analysis in the MS, and an action 250 of purifying and eluting the second analyte of interest for analysis in the MS.

In one embodiment, the first analyte of interest has a first log P and the second analyte of interest has a second log P that is different from the first log P. In one embodiment, the first and second log Ps may be separated by at least about 4.5 log P units. Suitable examples of analytes of interest that can be purified and analyzed using method 200 include, but are not limited to, vitamin D, steroid hormones, immunosuppressants, chemotherapeutics, tricyclic antidepressants, azole antifungals, anti-epileptics, anti-retrovirals, opiates and/or opioids, drugs of abuse, barbiturates, benzodiazepines, metabolites thereof, and combinations thereof. These analytes have log Ps ranging from about −1.2 (busulfin) to about 6 (25-OH vitamin $D_2$) (see, e.g., Table 1).

In one embodiment, the actions 210 and 220 can include providing two or more analytes selected from a first group and a second group, wherein the log partition coefficients (log P) of the first and second groups are separated by at least about 4.5 log P units. In another embodiment, the actions 210 and 220 can include providing a first analyte and a second analyte selected from the group consisting of vitamin D, steroid hormones, immunosuppressants, chemotherapeutics, tricyclic antidepressants, azole antifungals, anti-epileptics, anti-retrovirals, opiates and/or opioids, drugs of abuse, barbiturates, benzodiazepines, or a metabolite thereof, wherein the log partition coefficients (log P) of the first and second analytes are separated at least about 4.5 log P units. In yet another embodiment, the actions 210 and 220 can include providing a first analyte, a second analyte, and a third analyte, wherein the first analyte has a log partition coefficient (log P) in a range of about −1.2 to about 0, the second analyte has a log P in a range from about 0 to about 5, and the third analyte has a log P greater than about 5 and less than or equal to about 6.

Purifying and analyzing the first analyte of interest (240) followed by purifying an analyzing the second analyte of interest (250) is accomplished by varying at least one LC-MS system parameter selected from the group consisting of flow rate, composition of the mobile phase buffer solutions, a ratio of the aqueous mobile phase buffer solution to the non-aqueous mobile phase buffer solution, a gradient varying ratios of the aqueous and non-aqueous mobile phase buffer solutions, ionization voltage, desolvation temperature, lens amplitude, collision gas temperature, collision gas pressure, collision energy, and combinations thereof. Notably, purifying and analyzing the first analyte of interest (240) followed by purifying an analyzing the second analyte of interest (250) does not involve having to alter column or buffer selection.

In one embodiment, the additive included in the mobile phase buffers includes a source of ammonium ions. In one embodiment, the source of ammonium ions is ammonium formate or ammonium acetate. In one embodiment, the additive in the aqueous and non-aqueous mobile phase buffers includes about 2 mM to about 15 mM ammonium, about 2 mM to about 10 mM ammonium, or about 10 mM ammonium in the form of ammonium formate, ammonium acetate, or another suitable source of ammonium ions.

In one embodiment, the liquid chromatography system provided in action 230 is a high-performance liquid chromatography ("HPLC") system or an ultra high-performance liquid chromatography ("UHPLC") system. In one embodiment, the liquid chromatography system provided in action 230 includes a single sample clean-up liquid chromatography column (e.g., a Cyclone P column) and an analytical liquid chromatography column (e.g., e.g., a Hypersil Gold PFP, Accucore PFP™, Halo column). The sample clean-up liquid chromatography column and the analytical liquid chromatography column are in fluid communication with one another with the sample clean-up liquid chromatography column being upstream of the analytical liquid chromatography column. In one embodiment, the mass spectrometer includes an electrospray ionization (ESI) and/or an APCI ion source.

Ammonium ions in the form of ammonium formate, ammonium acetate, or another suitable source of ammonium ions may participate in the formation ions specific to each analyte of interest. For some analytes, ammonium ions may promote the formation of protonated ion form of the analyte of interest by donating a proton to the analyte either in the liquid phase or the gas phase. For some other analytes, (e.g., steroids) ammonium ions may promote the formation of ammoniated ions. In general, protonated and/or ammoniated molecular ions are preferred over water loss ions common in some ionization techniques because the analytes of interest have many possible routes for water loss, which can make water loss ions difficult to track in the mass spectrometer.

In one embodiment, the LC-MS system provided in action 230 further includes a sample handing device configured to manage a plurality of samples and a control system coupled to the LC-MS system and configured to control or vary at least one of a priority of analysis for the first sample and the second sample, flow rate, a ratio of the aqueous mobile phase buffer solution to the non-aqueous mobile phase buffer solution, a gradient varying ratios of the aqueous and non-aqueous mobile phase buffer solutions, ionization voltage, desolvation temperature, lens amplitude, collision gas temperature, collision gas pressure, and combinations thereof. The sample handling device and the control system are discussed in greater detail elsewhere in this application in the context of the system.

Figure 3:
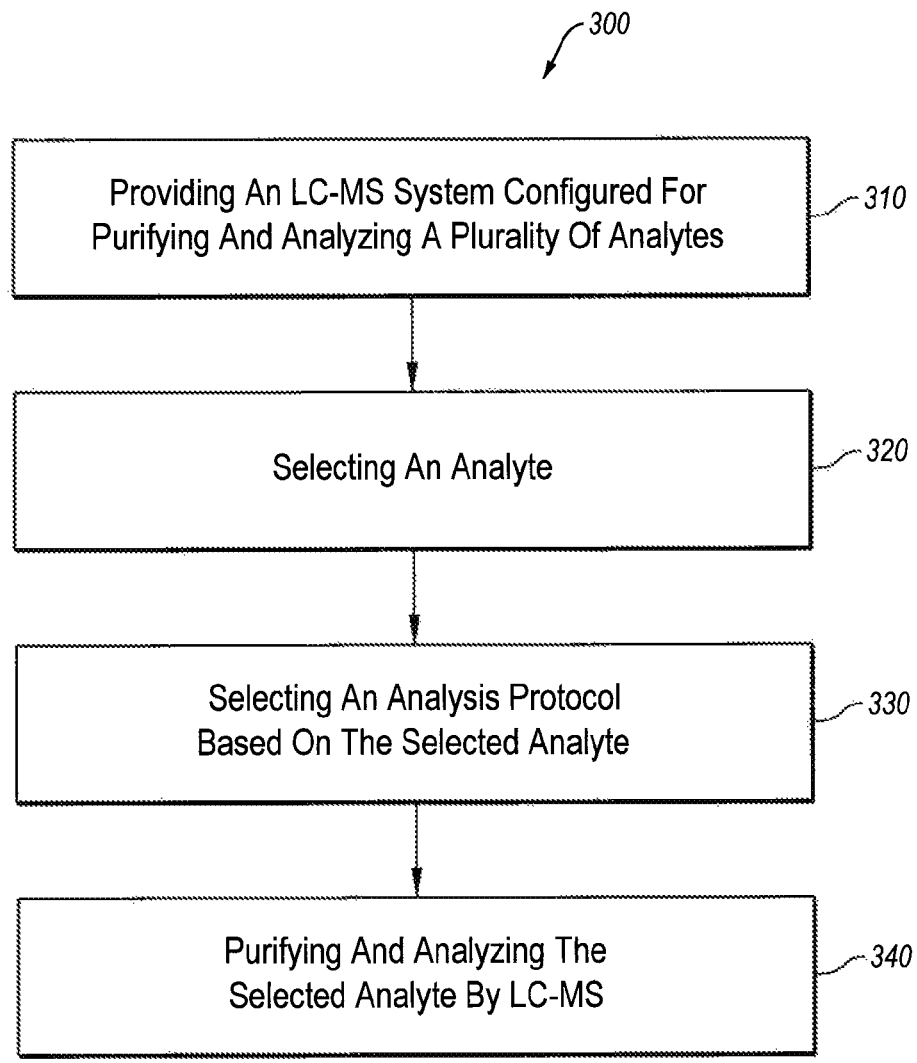
FIG. 3 is a flow diagram illustrating a method for purifying and analyzing analytes having a broad range of partition coefficients by liquid chromatography-mass spectrometry (LC-MS)

Referring now to FIG. 3, another method 300 for detecting and/or quantifying analytes having a wide range of partition coefficients using liquid chromatography-mass spectrometry (LC-MS) is illustrated. The method 300 includes an action 310 of providing an LC-MS system configured for purifying and analyzing a plurality of analytes of interest having partition coefficients (log P) spanning a range from about −1 to about 6, an action 320 of selecting a sample containing a selected analyte of interest, an action 330 of selecting an analysis protocol based on the selected analyte of interest, and an action 340 of purifying, eluting, and analyzing the selected analyte of interest by LC-MS.

In one embodiment, the action 300 includes providing a single analytical liquid chromatography column of a liquid chromatography-mass spectrometry (LC-MS) system, one aqueous mobile phase buffer solution of the LC-MS system, and one substantially non-aqueous mobile phase buffer solution of the LC-MS. The LC-MS system is configured for purifying and analyzing a plurality of analytes having a log partition coefficients (log P) spanning a range of about −1.2 to about 6 by varying at least one LC-MS system parameter. LC-MS system parameters include, but are not limited to, mobile phase buffer flow rate, a ratio of an aqueous mobile phase buffer solution to a non-aqueous mobile phase buffer solution, a gradient varying ratios of the aqueous and non-aqueous mobile phase buffer solutions, ionization voltage, desolvation temperature, electrode voltage, collision gas temperature, collision gas pressure, collision energy, and combinations thereof.

EXAMPLES

Example 1

Purification and Analysis of 25-OH Vitamin $D_2$ and 25-OH Vitamin $D_3$ 25-hydroxyvitamin $D_3$ and 25-hydroxyvitamin $D_2$ were purchased from Sigma (St. Louis, Mo.). A 2 mg/mL stock solution was made by dissolving 25-hydroxyvitamin $D_3$ and 25-hydroxyvitamin $D_2$ in methanol. All other concentrations were made by serial dilutions into methanol (neat) or stripped serum (matrix) such as charcoal-stripped fetal bovine serum (Sigma Aldrich, Cat. No. F6765) or antibody-stripped human serum. Standards and QCs were made in stripped serum. Standards were made with a range of 1-300 ng/mL and QCs were made 2, 120 and 240 ng/mL. Hexa-deuterated 25-hydroxyvitamin $D_3$ (d6-25-OH D3) was purchased from Medical Isotopes (Cat. No. D2831) and used as an internal standard (IS). A 1 mg/mL IS stock solution was made in methanol and diluted to 140 ng/mL with methanol for the working IS stock solution. All stock and working solutions were stored at −80° C.

Samples were prepared by adding 200 µL of working internal standard to 100 µL of sample followed by vortex mixing for 15 sec at max speed and centrifugation at 4000 rcf for 2 min. 150 µL of supernatant was then transferred into autosampler vials for analysis.

HPLC was performed with Thermo Scientific Transend TX system (Thermo Fisher Scientific) using a 0.5×50 mm Cyclone P column (Thermo Fisher Scientific) for on-line sample clean-up and a 2.1×50 mm, 1.9 µm Hypersil Gold PFP or 2.1×50 mm, 2.6 µm Accucore PFP™ analytical column (Thermo Fisher Scientific). This system is a dual column system that can perform Ultra High Pressure Liquid Chromatography (UHPLC) and utilizes TurboFlow technology to perform on-line clean-up. The mass spectra were acquired on a Thermo Scientific Vantage triple quadrupole mass spectrometer (Thermo Fisher Scientific). Mobile phase A was 10 mM ammonium formate with 0.01% formic acid in water. Mobile phase B was 10 mM ammonium formate with 0.01% formic acid in methanol. Mobile phase C was 45:45:10 isopropanol:acetonitrile:acetone that is used to wash the columns.

10 μL of sample was injected onto the turbulent flow chromatography ("TFC") column with 80% mobile phase A at 1.5 mL/min Large molecules, such as proteins, are washed to waste while small molecules (>1000 Da) are retained on the column. Once the sample has been separated from most of the biological matrix, the valves switch and the sample is eluted from the TFC column with 100% mobile phase B at 0.2 mL/min. The flow from the TFC column is teed to a second UHPLC pump flowing 80% mobile A at 0.5 mL/min. The mixed flow from both pumps reduces the amount of organic seen by the analytical column such that the analyte of interest is focused at the head of the analytical column. Once the analyte of interest is transferred to the analytical column, the valves are switched again, isolating the two columns from each other. The TFC column is washed and equilibrated for the next sample and a 20-100% mobile phase B gradient is run on the analytical column to elute the analyte of interest into the mass spectrometer for analysis.

The mass spectrometer parameters are as follows: Spray voltage 5000, Vaporizer temperature 400, sheath gas pressure 60, aux gas pressure 35, capillary temperature 199, S-lens amplitude 55. Full scan Q1 data was acquired to look at the relative ion abundances of the methods tested and Selective Reaction Monitoring (SRM) was used for quantitative comparison.

The SRM transitions used were as follows; 25-hydroxyvitamin $D_3$: 401.352 parent, 91.122, 105.133, 159.139, 365.425 product ions. 25-hydroxyvitamin $D_2$: 91.089, 95.158, 105.104, 159.149 product ions. $d_6$-25-OH $D_3$: 407.380 parent, 107.115, 133.105, 147.199, 159.190 product ions. Quadrupole 1 (Q1) (full width at half maximum, FWHM) was set at 0.2 and quadrupole 3 (Q3) (FWHM) was set at 0.7. Scan width (Dale) 0.01, scan time (s) 0.05. Collision gas pressure was set at 1.5 mTorr.

Figures 4A, 4B:
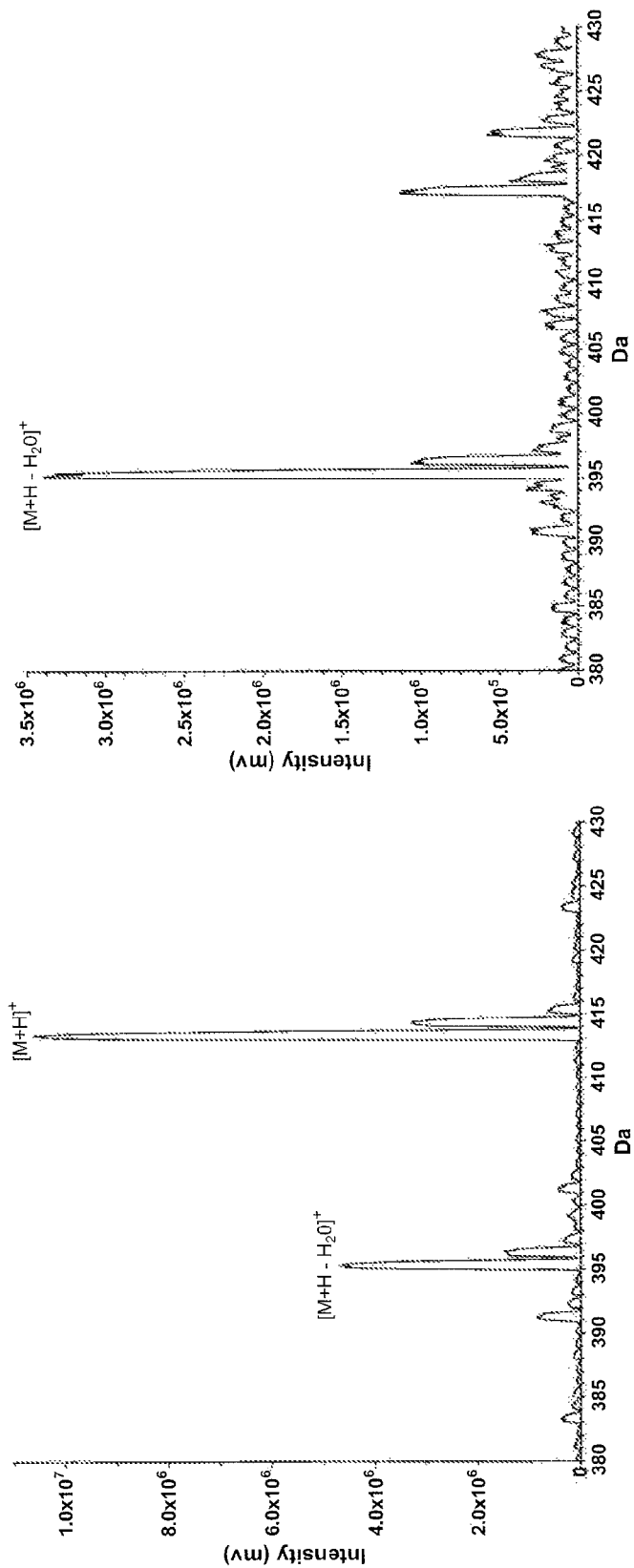
FIG. 4A depicts an ESI full scan spectrum of the molecular ion region for 25-OH $D_2$ using ammonium formate.
FIG. 4B depicts an ESI full scan spectrum of the molecular ion region for 25-OH $D_2$ using formic acid.
Figure 6:
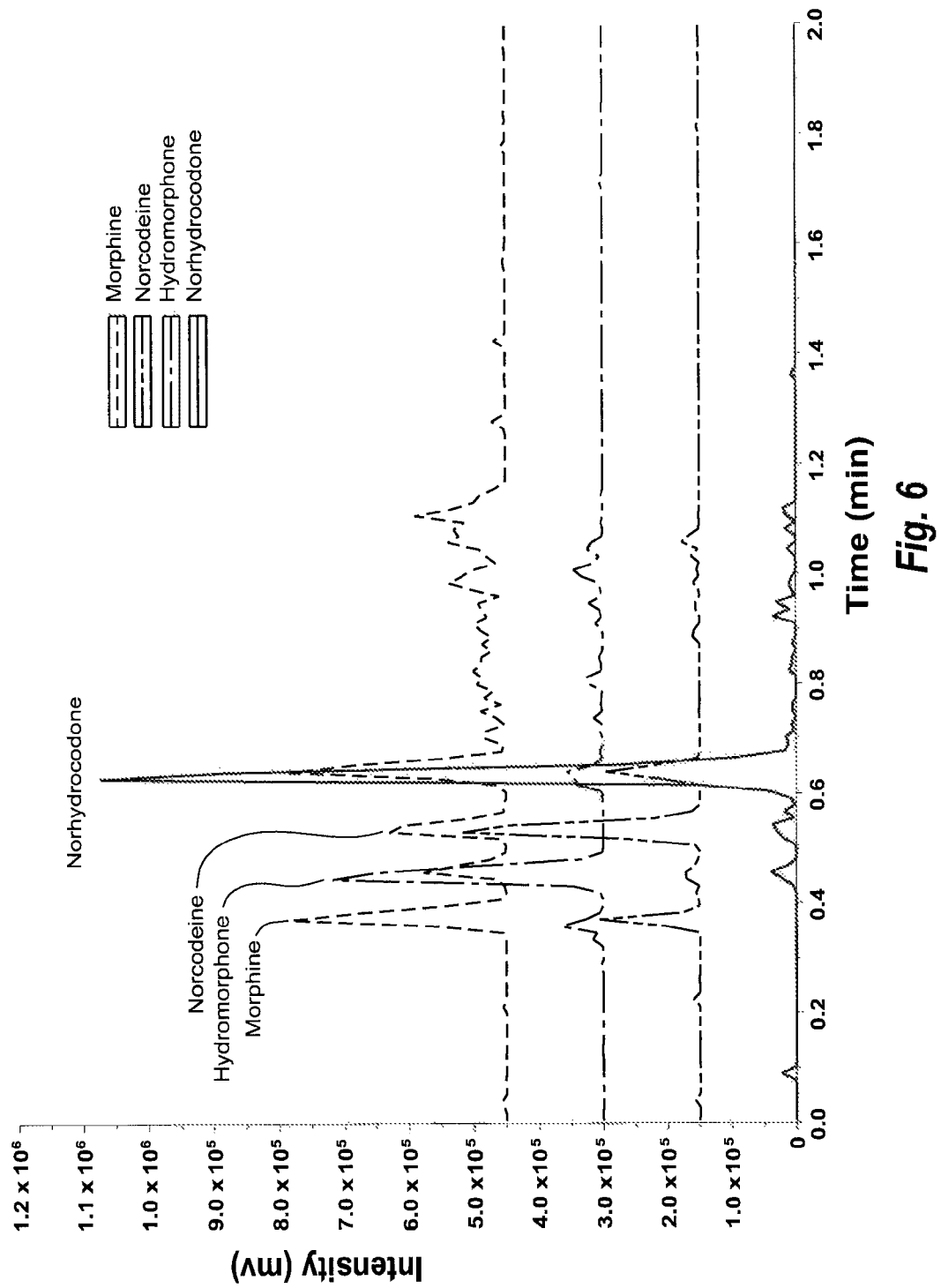
FIG. 6 depicts MRM chromatograms from an injection of a solution containing morphine, norcodeine, hydromorphone, and norhydrocodone.
Figure 7:
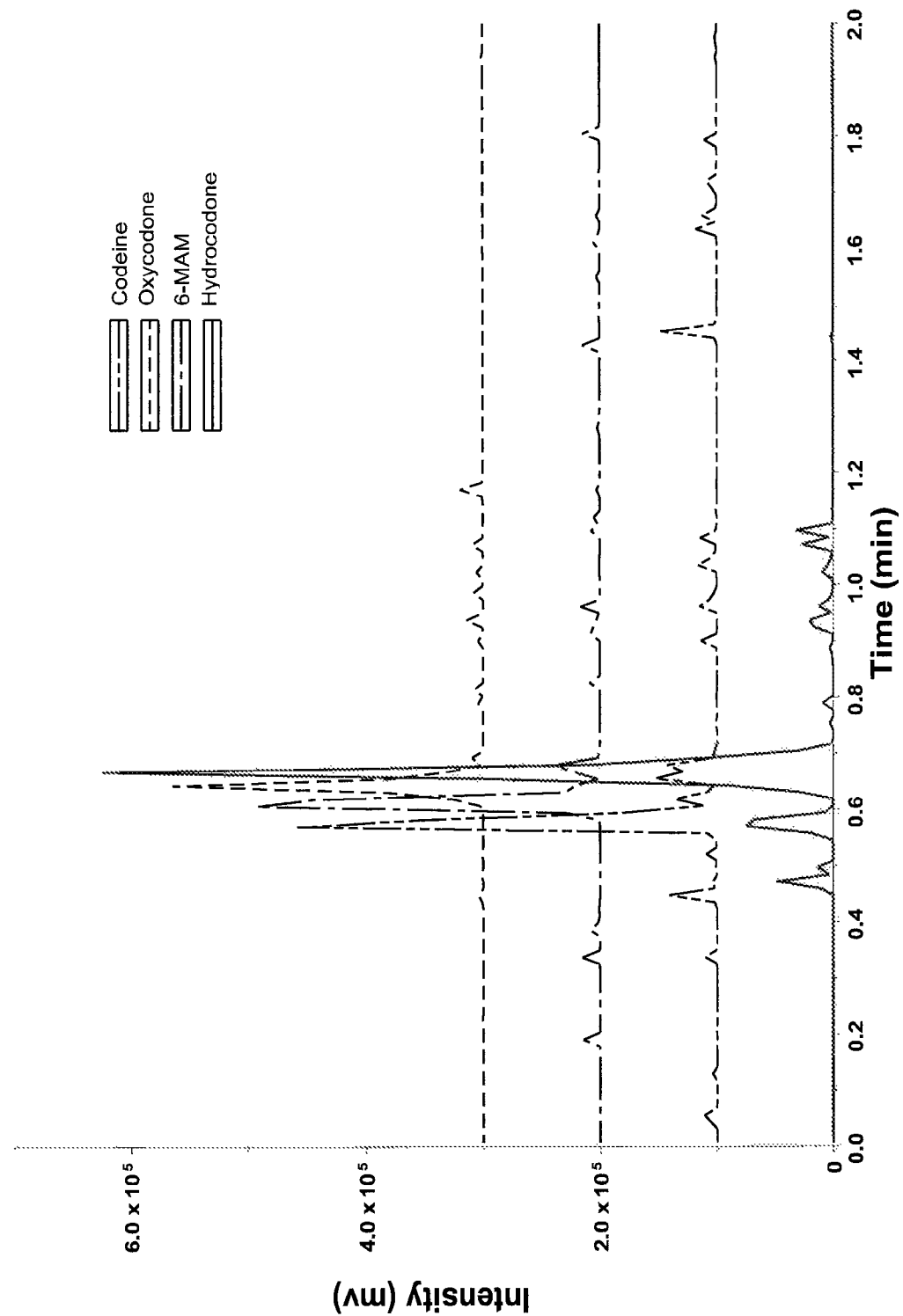
FIG. 7 depicts MRM chromatograms from an injection of a solution containing of codeine, oxycodone, 6-monoacetylmorphine (6-MAM), and hydrocodone.
Figure 8:
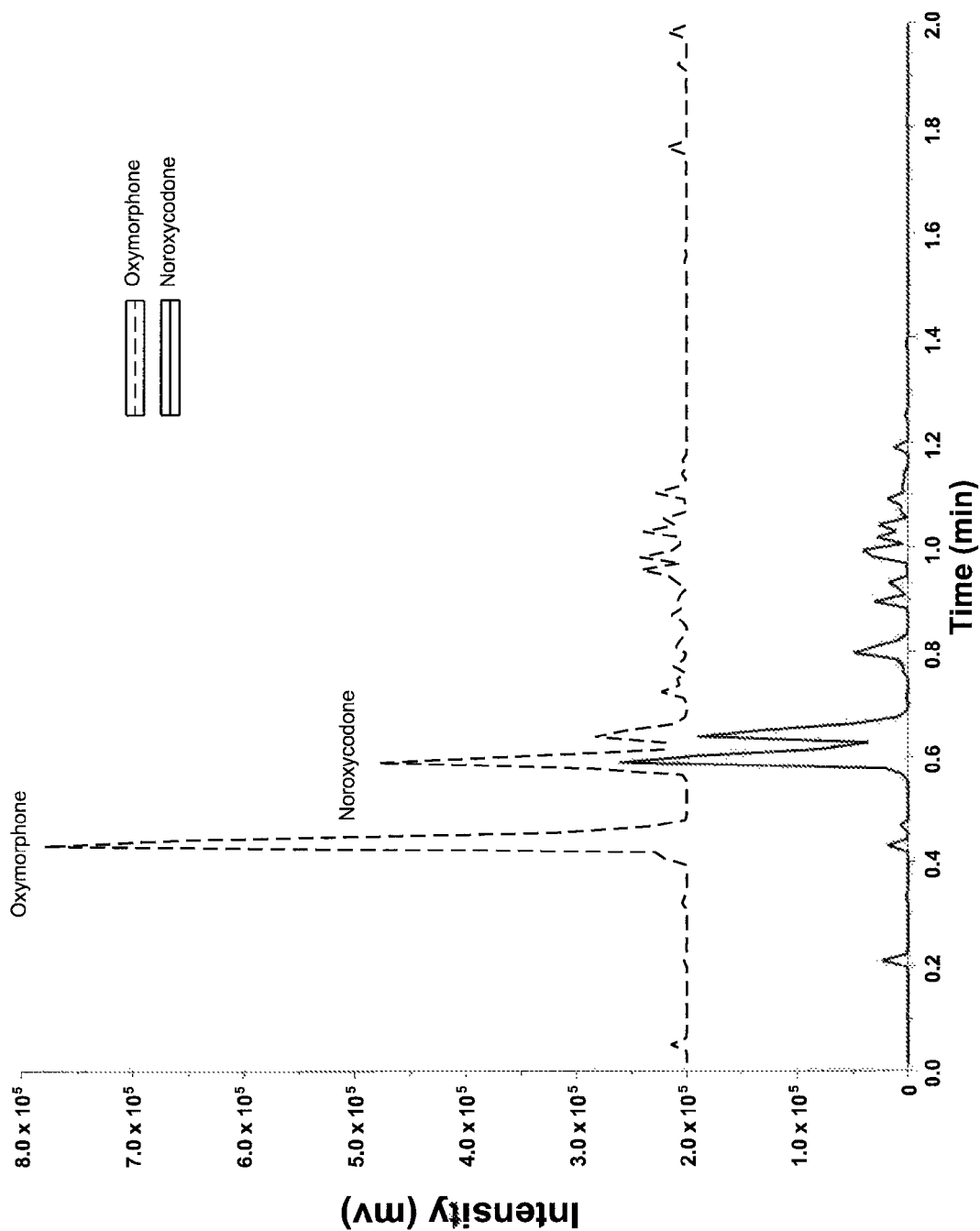
FIG. 8 depicts MRM chromatograms from an injection a solution containing oxymorphone and noroxycodone.
Figure 9:
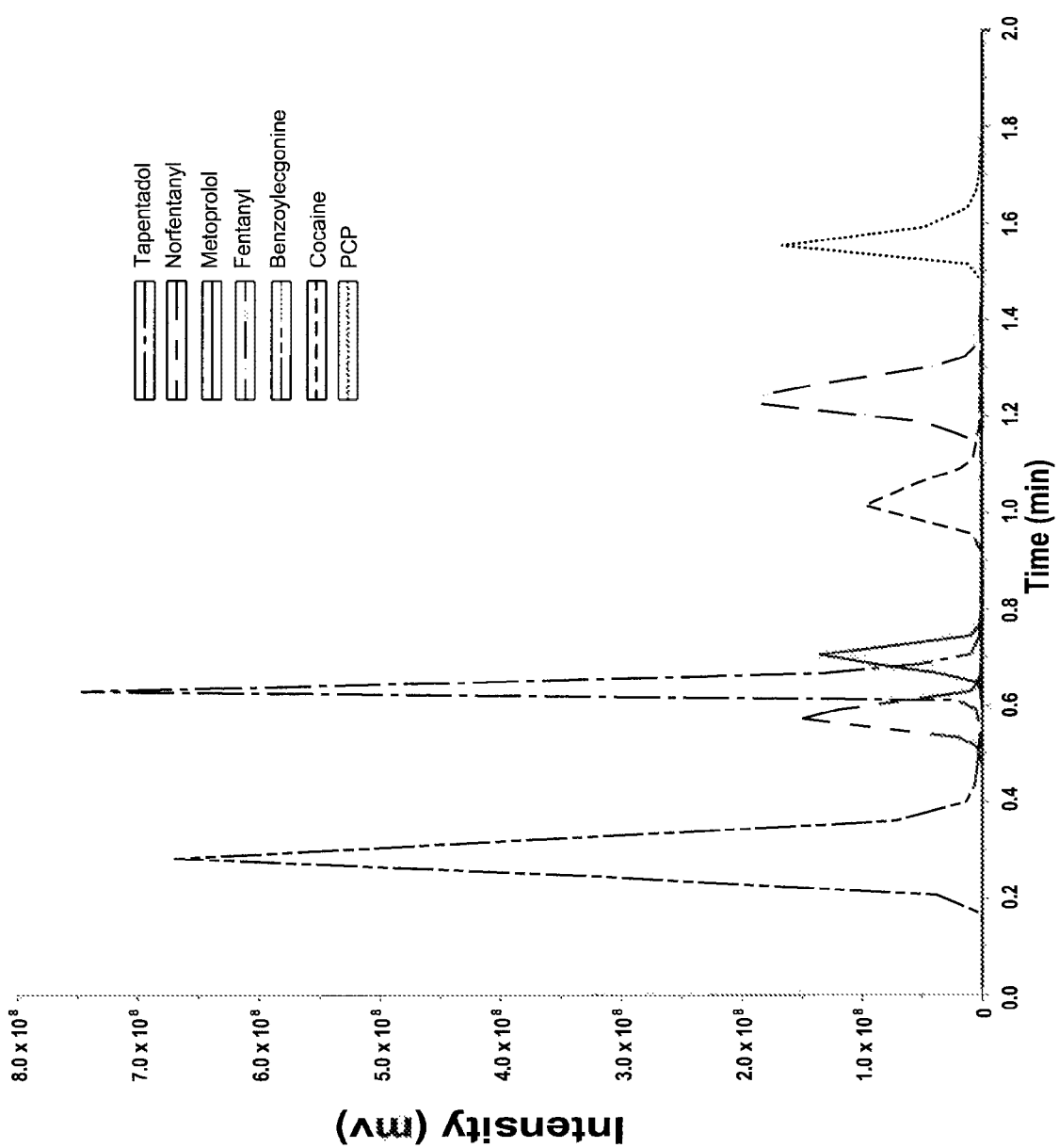
FIG. 9 depicts MRM chromatograms from an injection of a solution containing tapentadol, norfentanyl, metoprolol, fentanyl, benzoylecgonline, cocaine, and phencyclidine (PCP)
Figure 10:
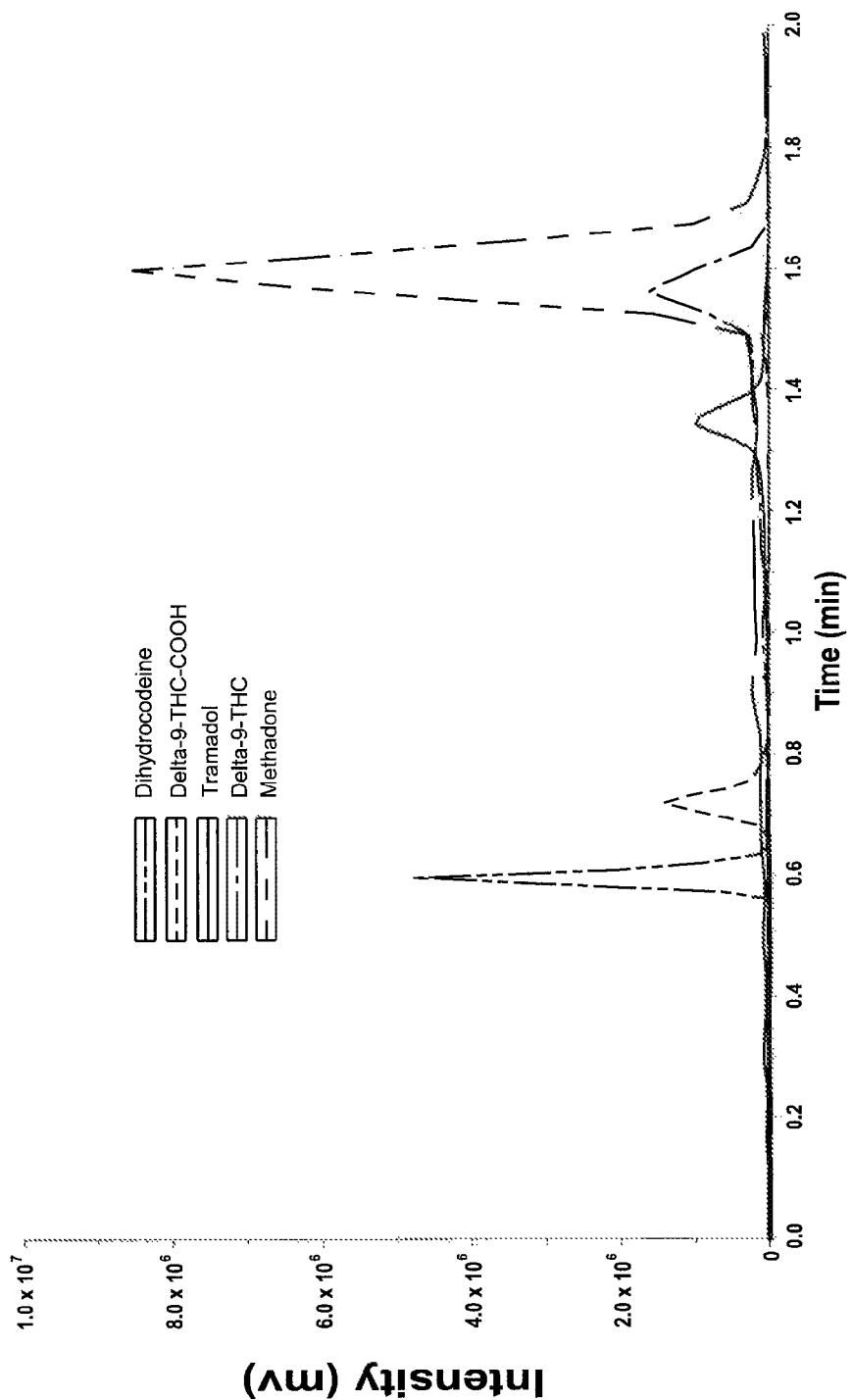
FIG. 10 depicts MRM chromatograms from an injection of a solution containing dihydrocodeine, $d^9$-THC-COOH, $d^9$-THC, tramadol, and methadone.
Figure 11:
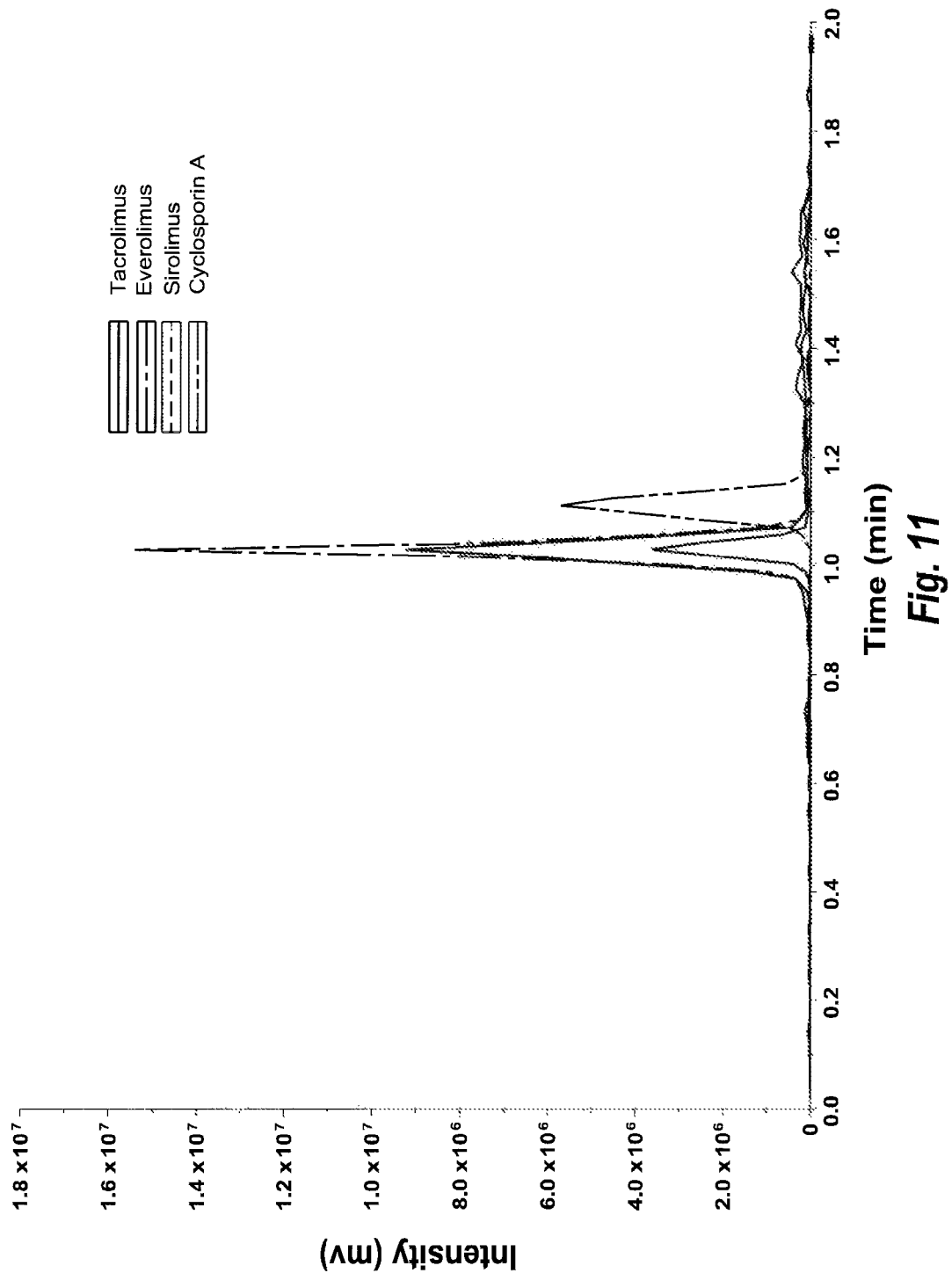
FIG. 11 depicts MRM chromatograms from an injection of a solution containing the immunosuppressant drugs tacrolimus, everolimus, sirolimus, and cyclosporine A.
Figure 12:
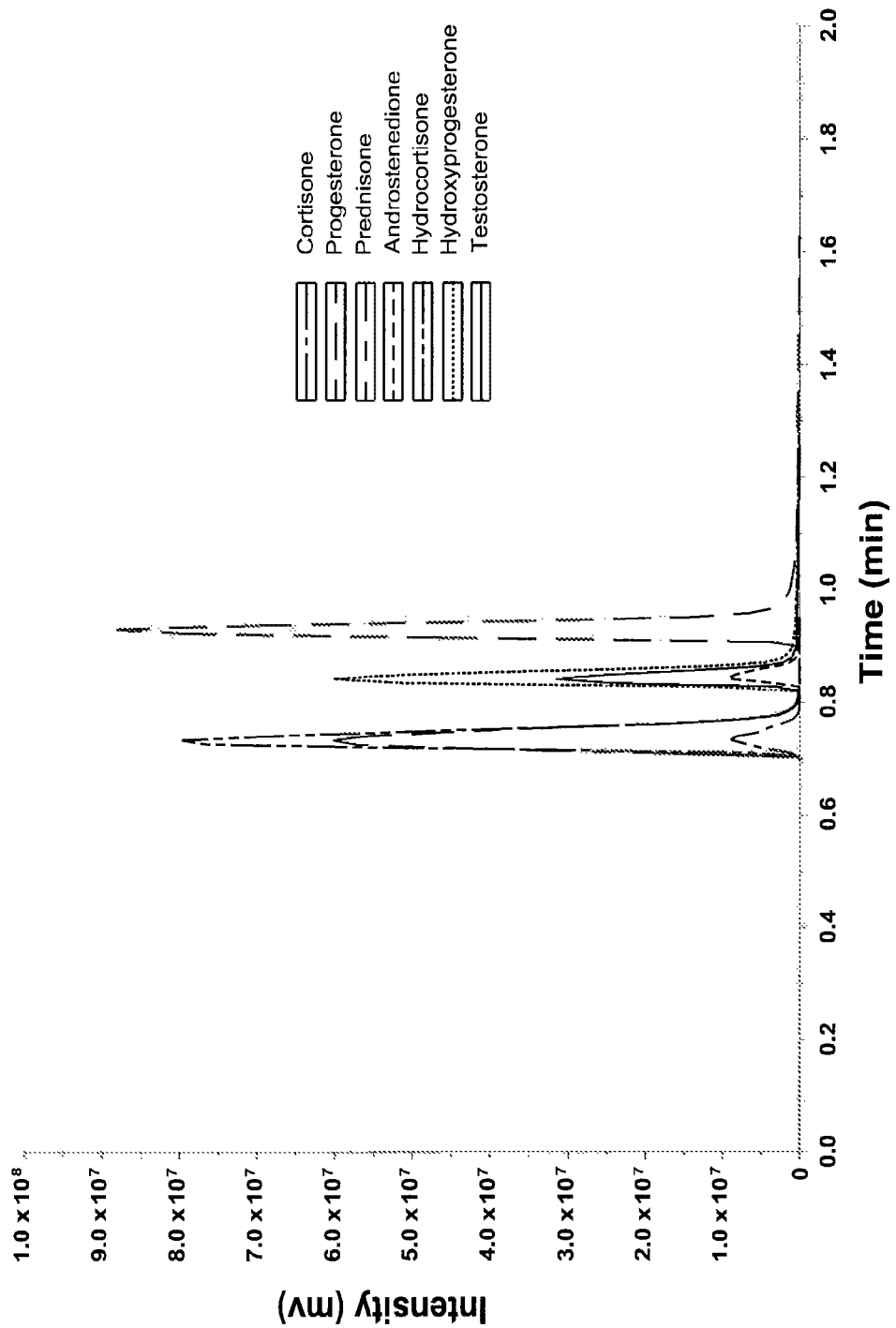
FIG. 12 depicts MRM chromatograms from an injection of a solution containing the steroids cortisone, progesterone, prednisone, androstenedione, cortisol (hydrocortisone), hydroxyprogesterone, and testosterone.
Figure 13:
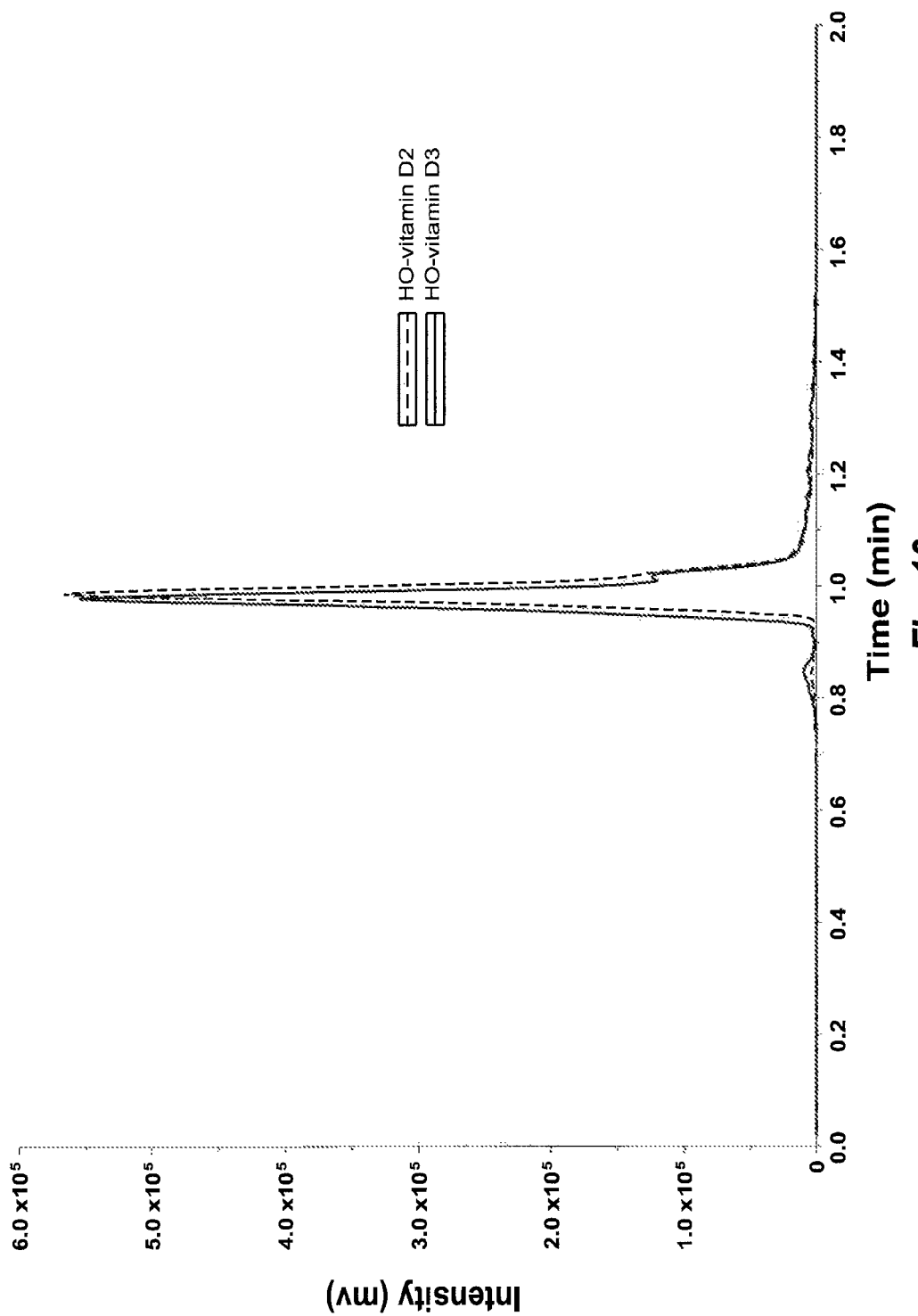
FIG. 13 depicts MRM chromatograms from an injection of a solution containing 25-hydroxy vitamin $D_2$ and $D_3$.
Figure 14:
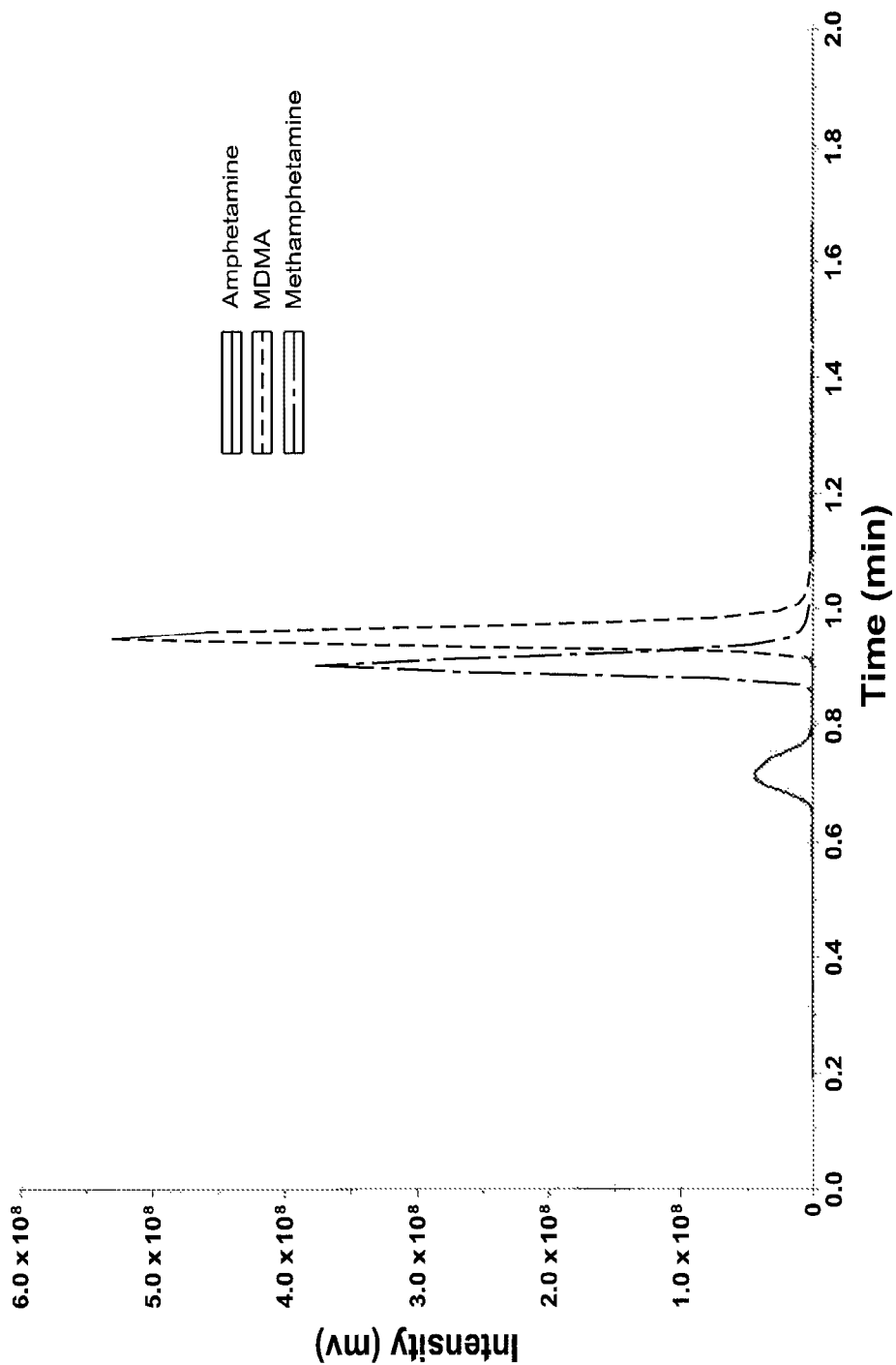
FIG. 14 depicts MRM chromatograms from an injection of a solution containing the amphetamines amphetamine, MDMA, and methamphetamine.
Figure 15:
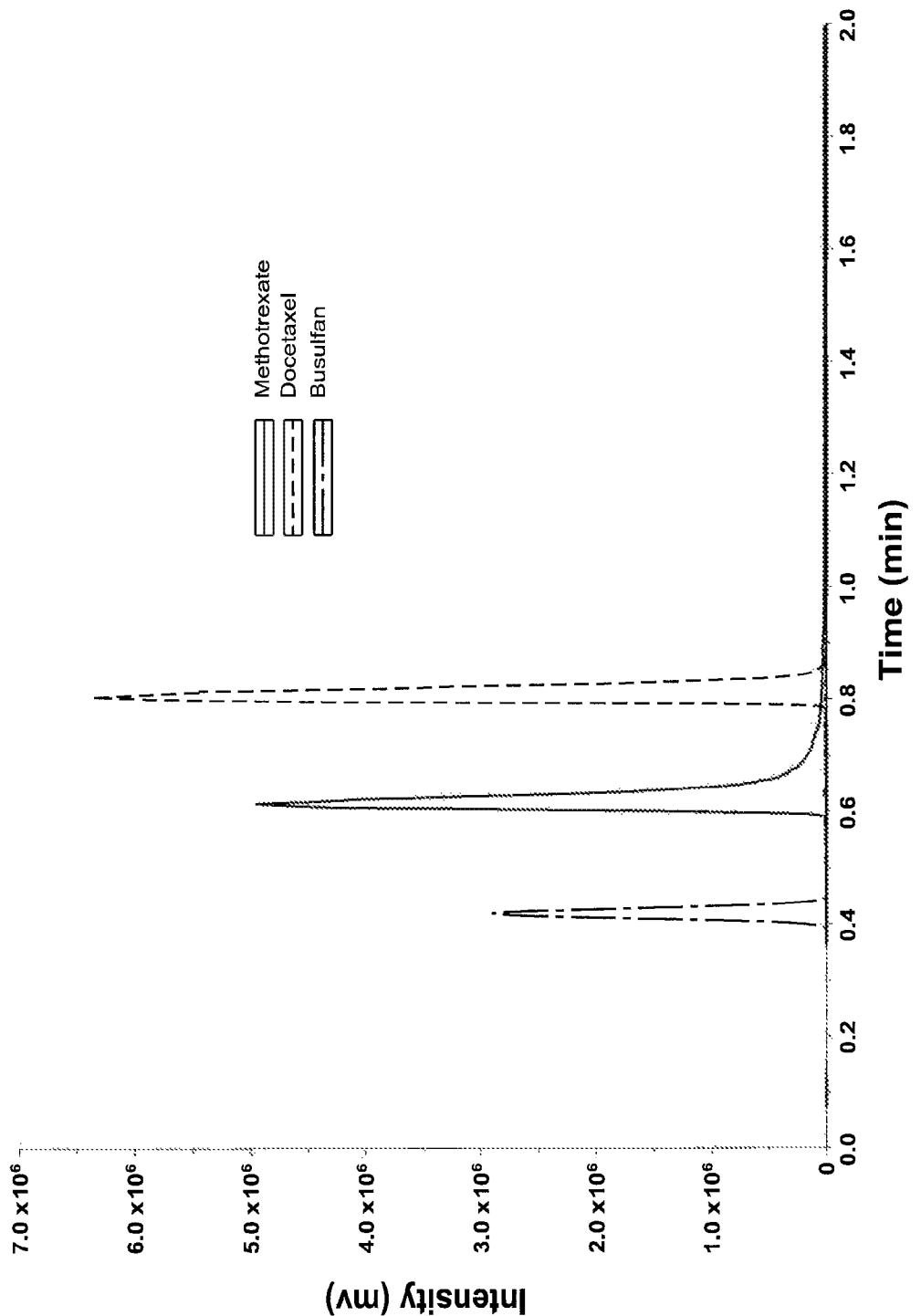
FIG. 15 depicts MRM Chromatograms from an injection of a solution containing the chemotherapeutic drugs methotrexate, docetaxcel, and busulfin.
Figure 16:
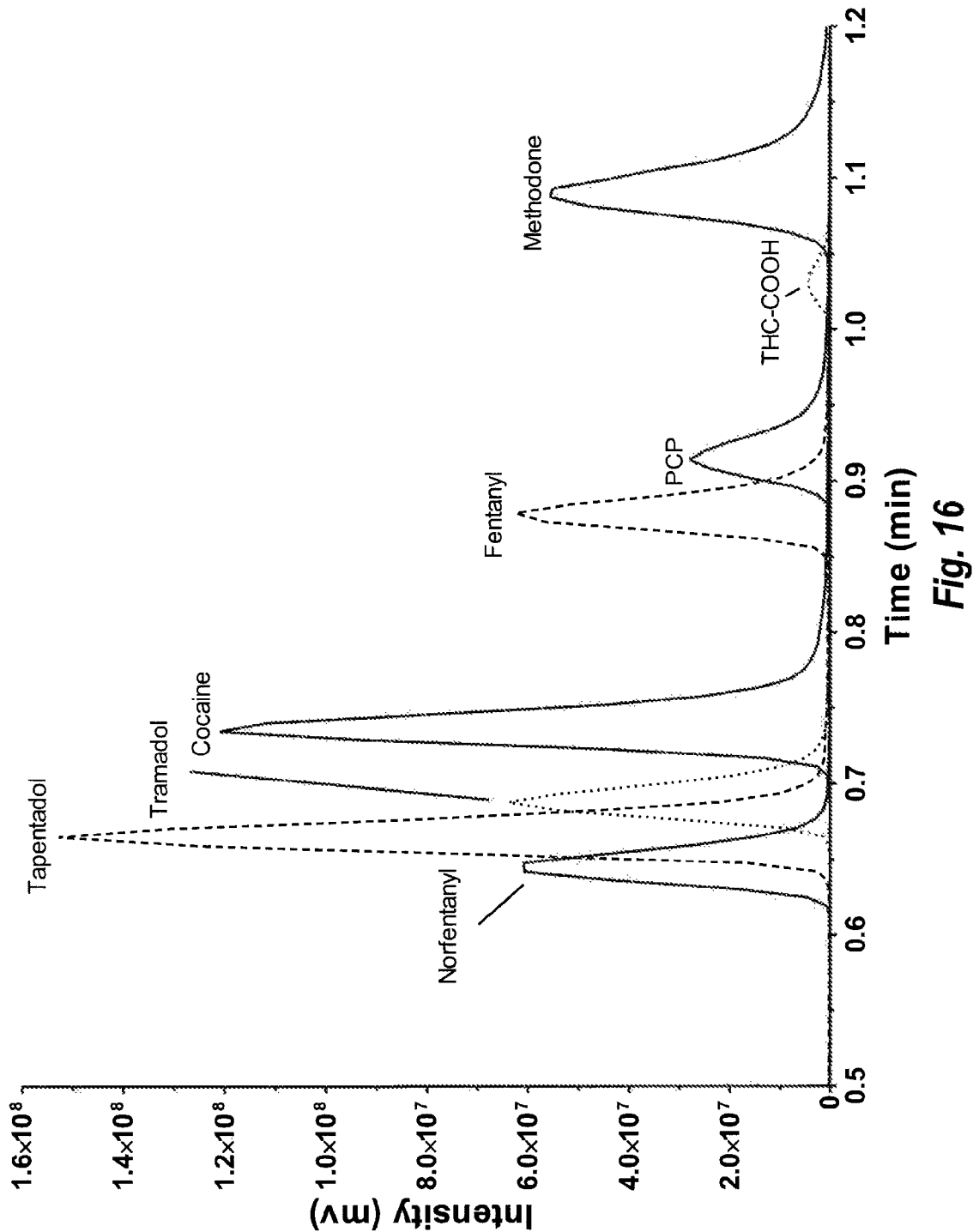
FIG. 16 depicts MRM chromatograms from an injection of an antibody-stripped serum solution containing norfentanyl, tapentadol, tramadol, cocaine, fentanyl, PCP, THC-COOH, and methadone.
Figure 17:
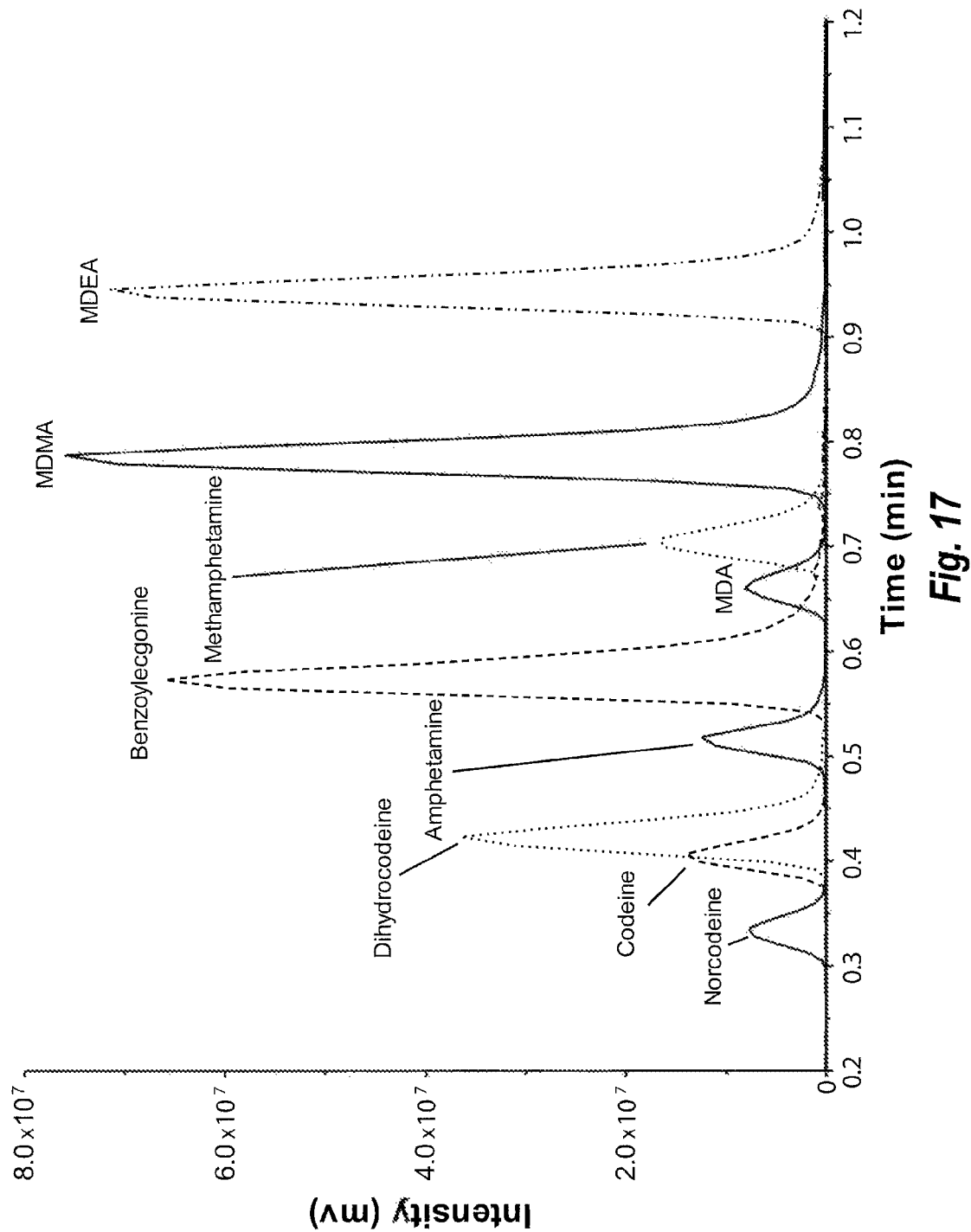
FIG. 17 depicts MRM chromatograms from an injection of an antibody-stripped serum solution containing norcodeine, codeine, dihydrocodeine, amphetamine, benoylecgonine, MDA, methamphetamine, MDMA, and MDEA.
Figure 18:
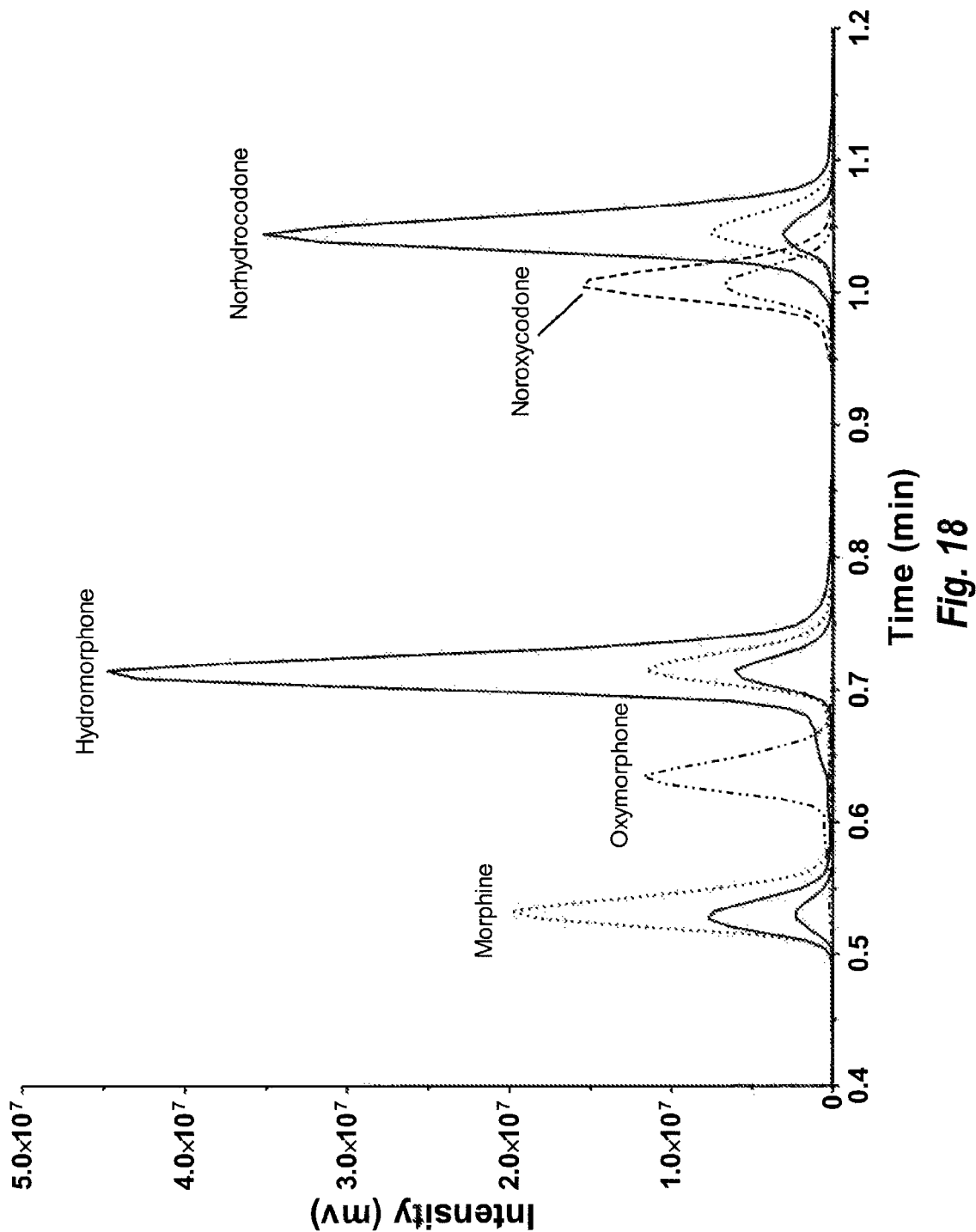
FIG. 18 depicts MRM chromatograms from an injection of an antibody-stripped serum solution containing morphine, oxymorphone, hydromophone, noroxycodone, and norhydrocodone.
Figure 19:
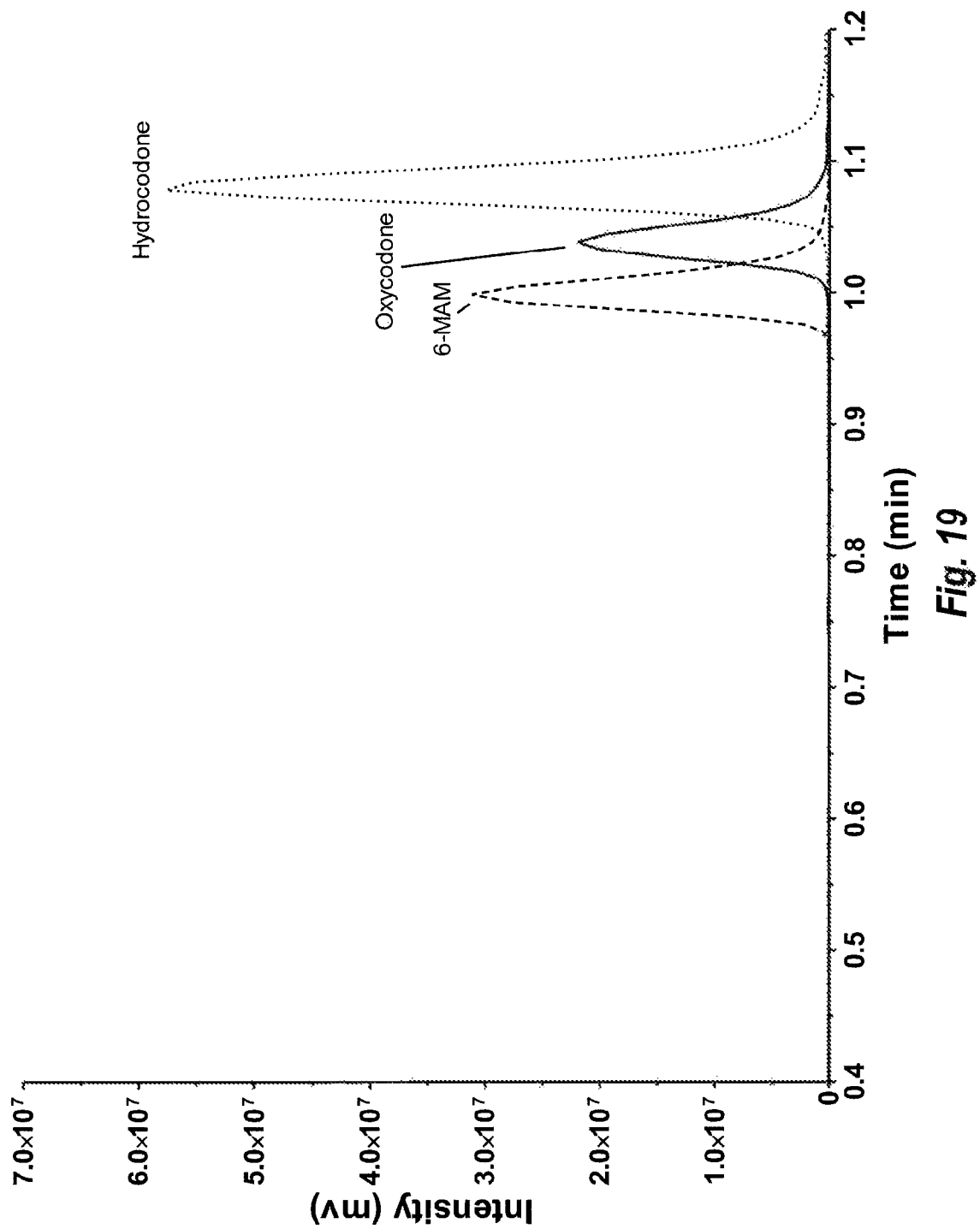
FIG. 19 depicts MRM chromatograms from an injection of an antibody-stripped serum solution containing 6-MAM, oxycodone, and hydrocodone.
Figure 20:
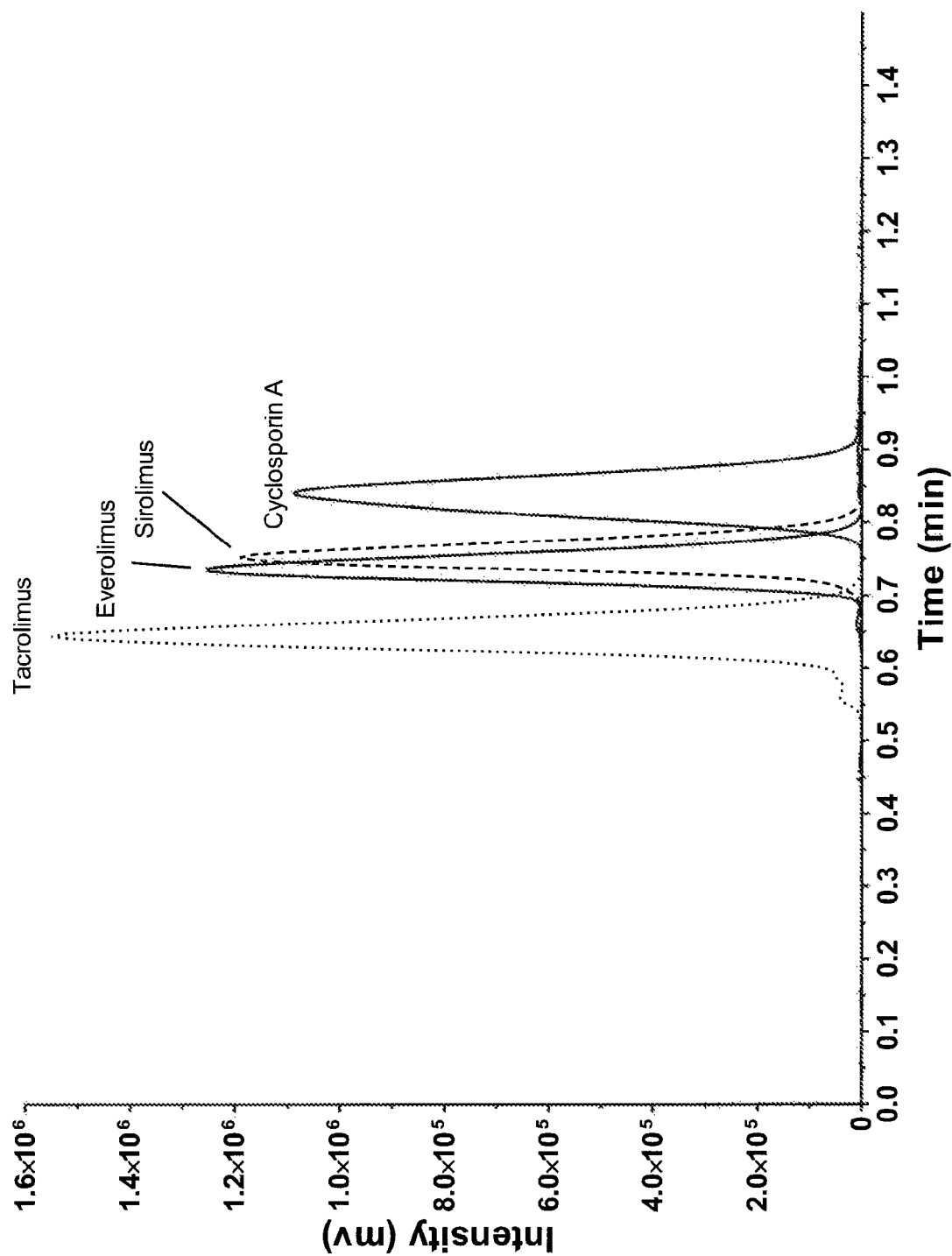
FIG. 20 depicts MRM chromatograms from an injection of an antibody-stripped serum solution containing tacrolimus, everolimus, sirolimus, and cyclosporin A.
Figure 21:
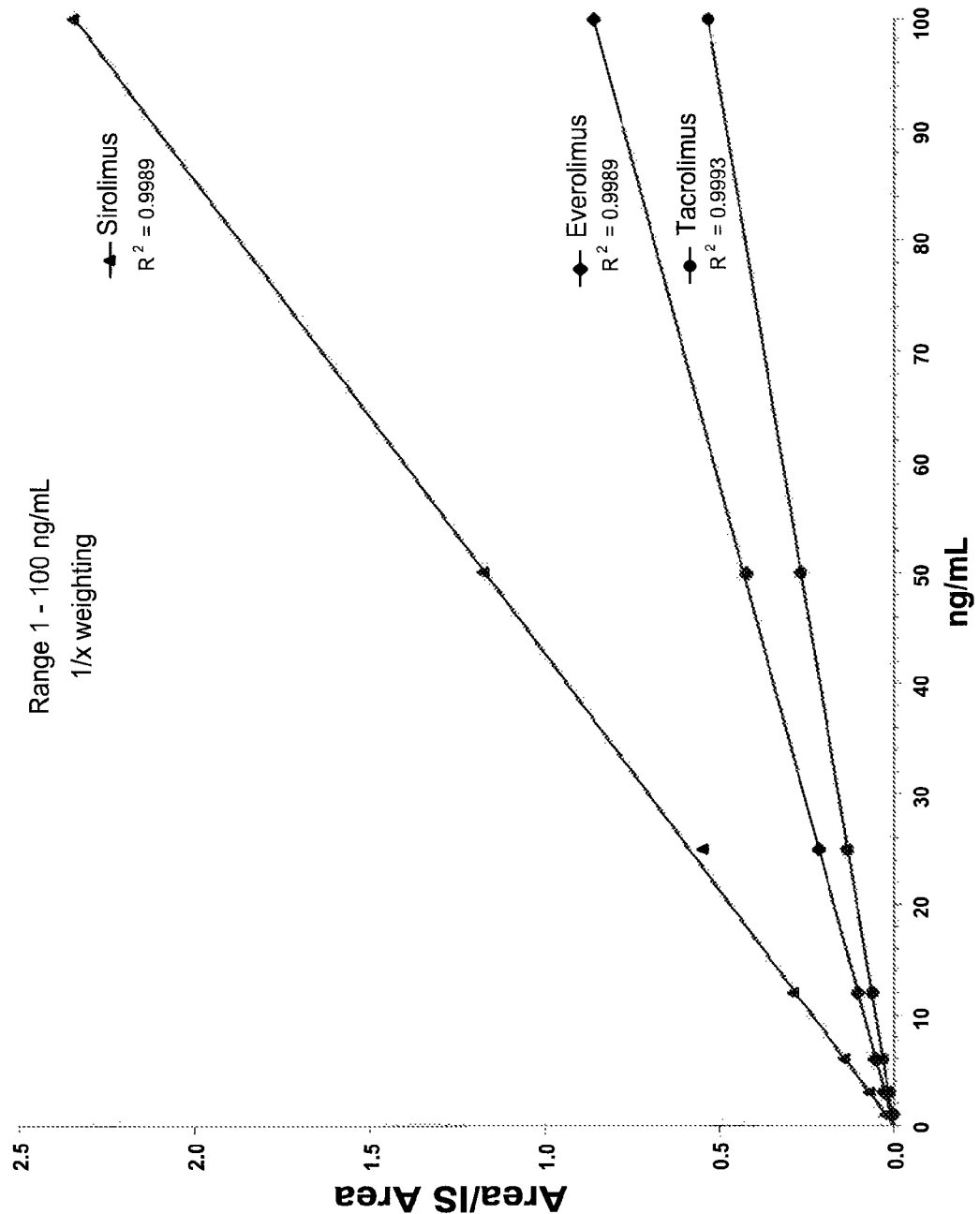
FIG. 21 depicts standard curves generated from a whole blood solution containing the immunosuppressant drugs tacrolimus, everolimus, and sirolimus.
Figure 22:
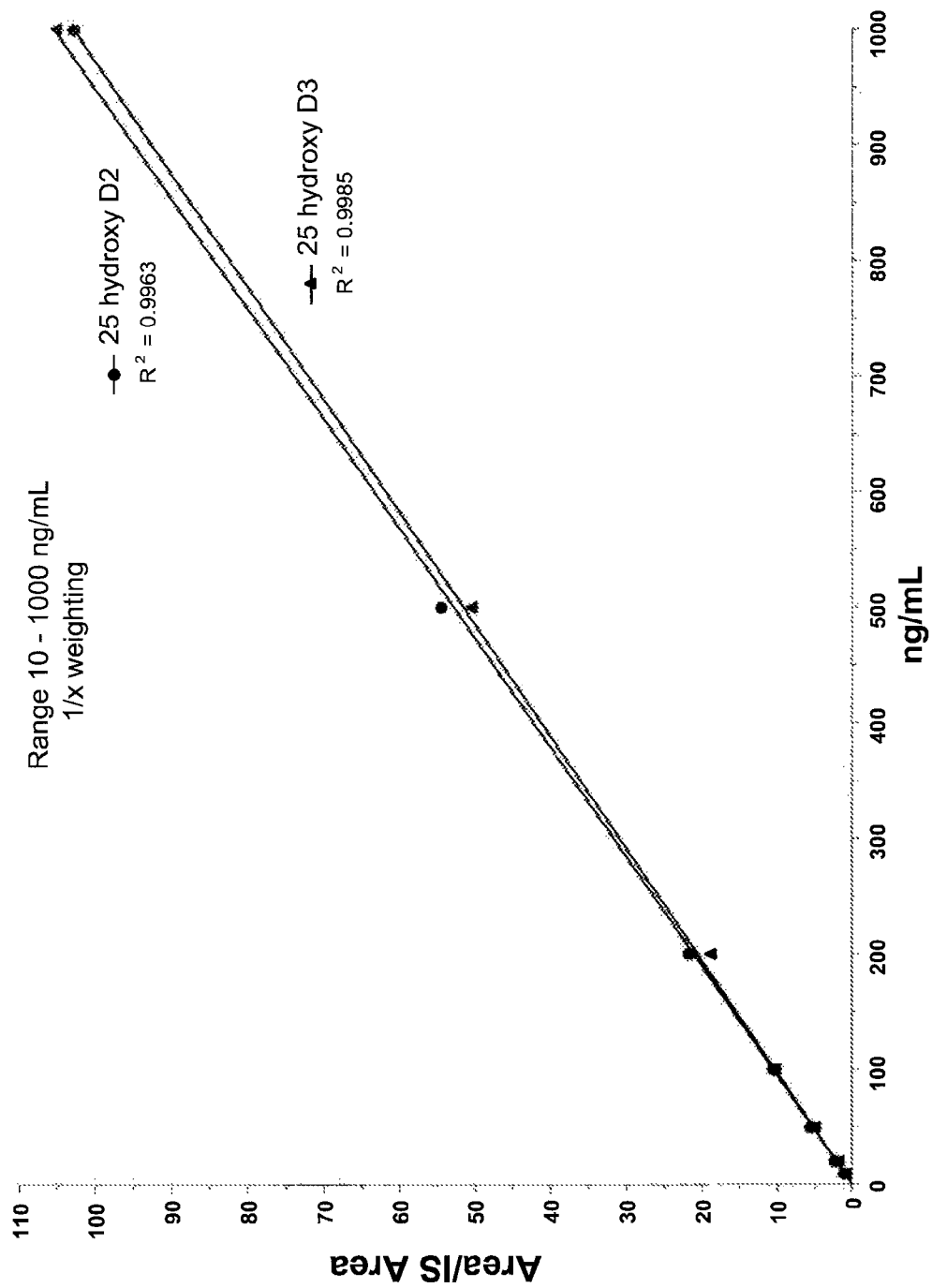
FIG. 22 depicts standard curves generated from a plasma solution containing 25-hydroxy Vitamin $D_2$ and $D_3$.
Figure 23:
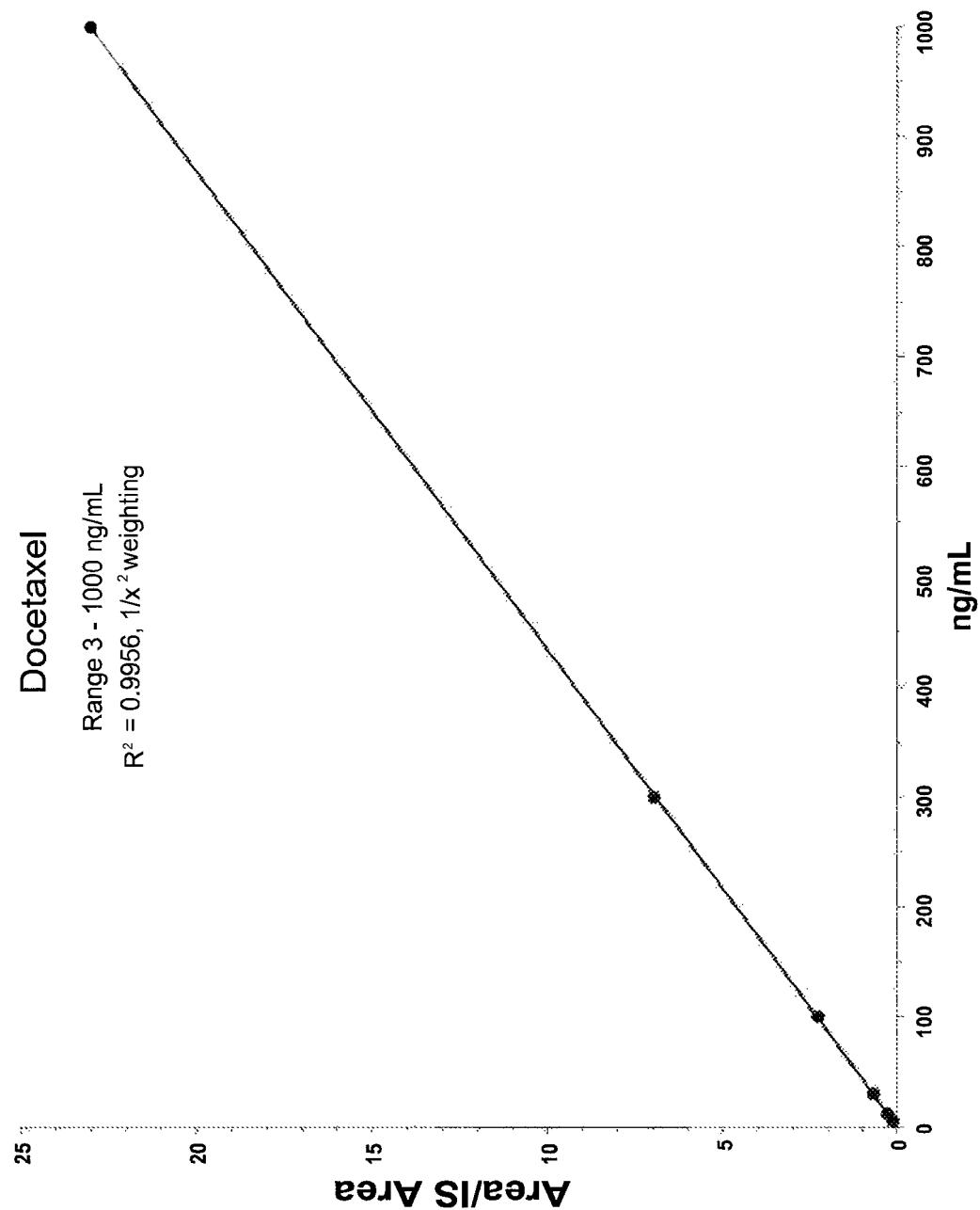
FIG. 23 depicts a standard curve for docetaxcel in plasma.
Figure 24:
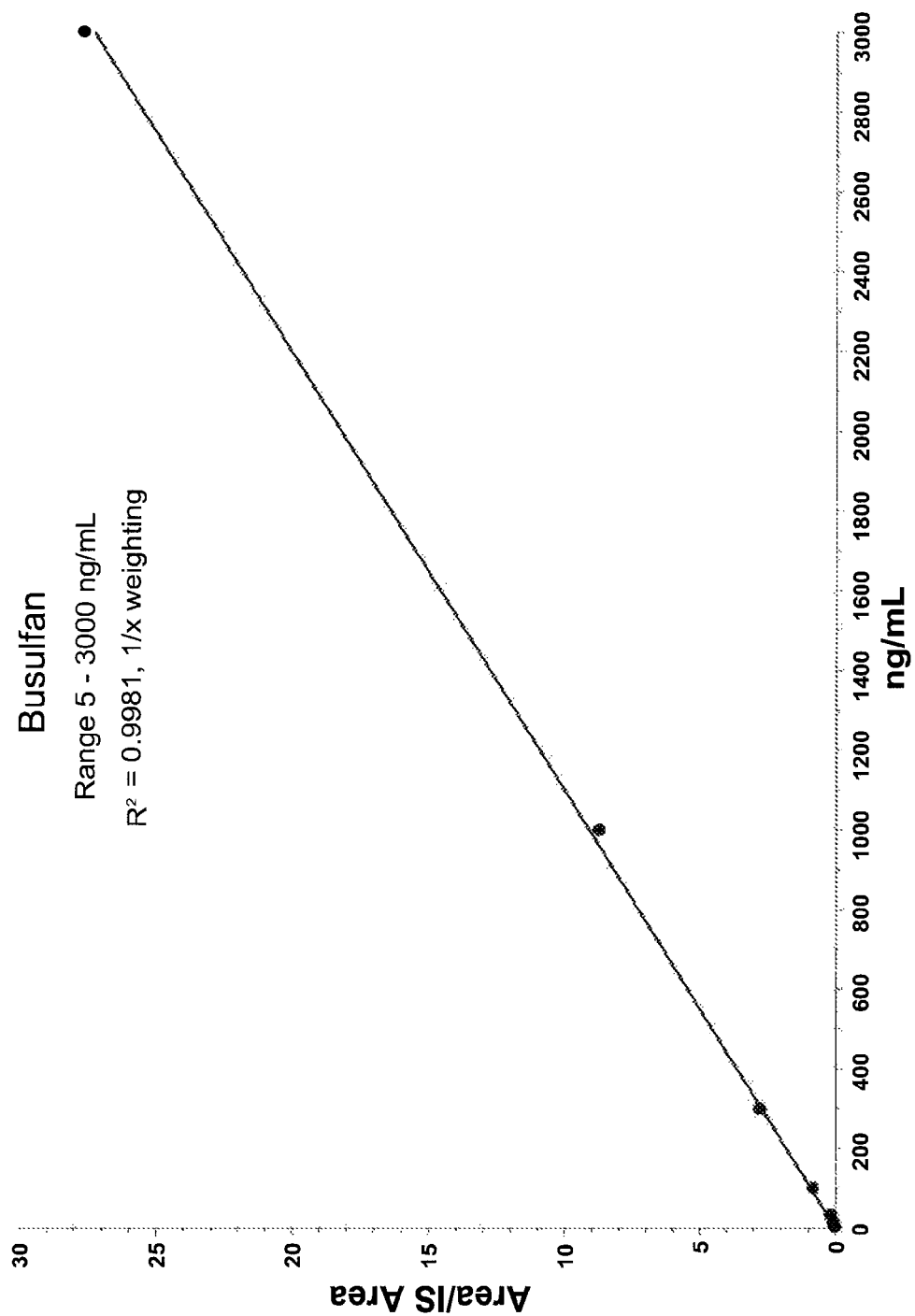
FIG. 24 depicts a standard curve for busulfin in plasma
Figure 25:
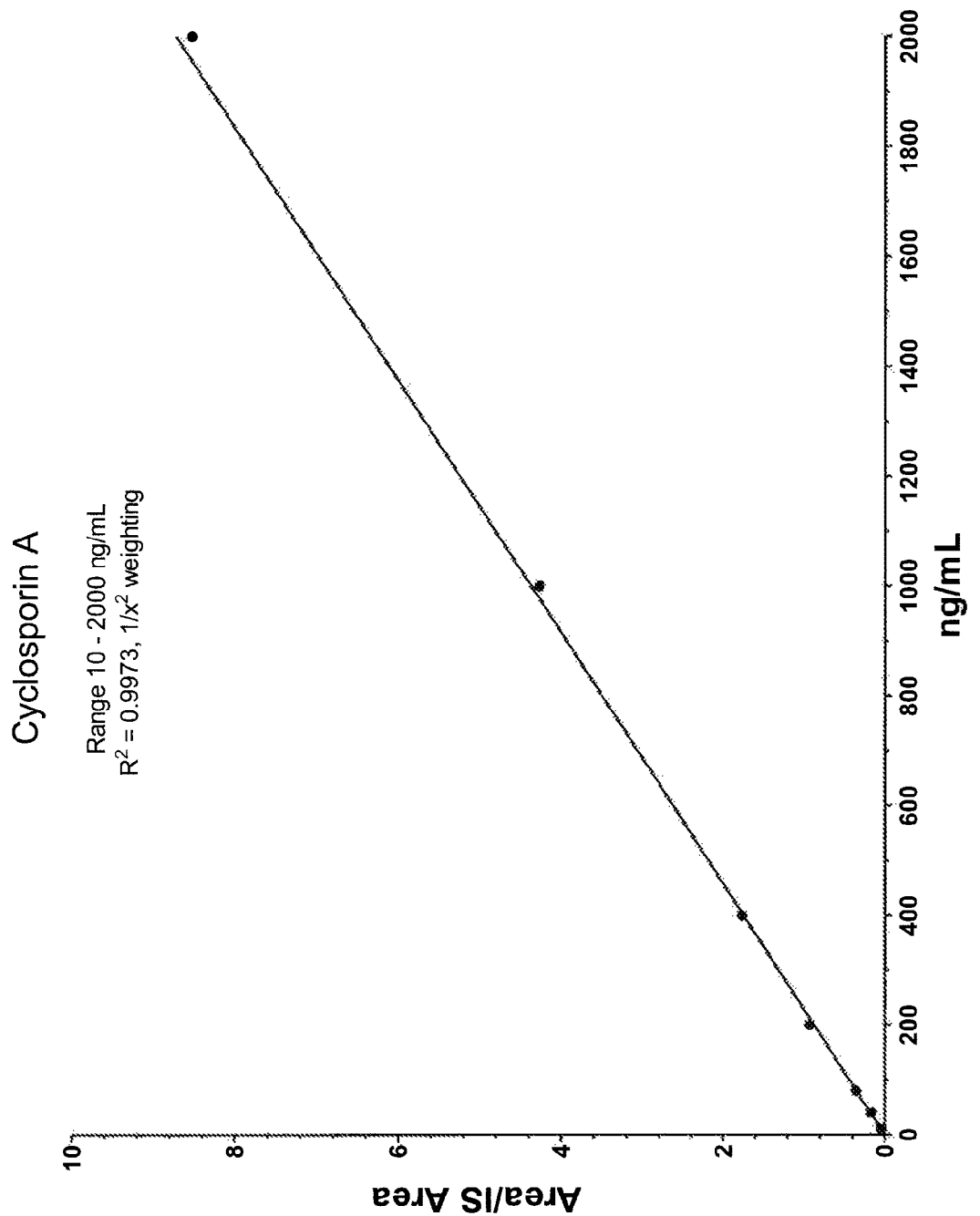
FIG. 25 depicts a standard curve for cyclosporin A in antibody-stripped serum.
Figure 26:
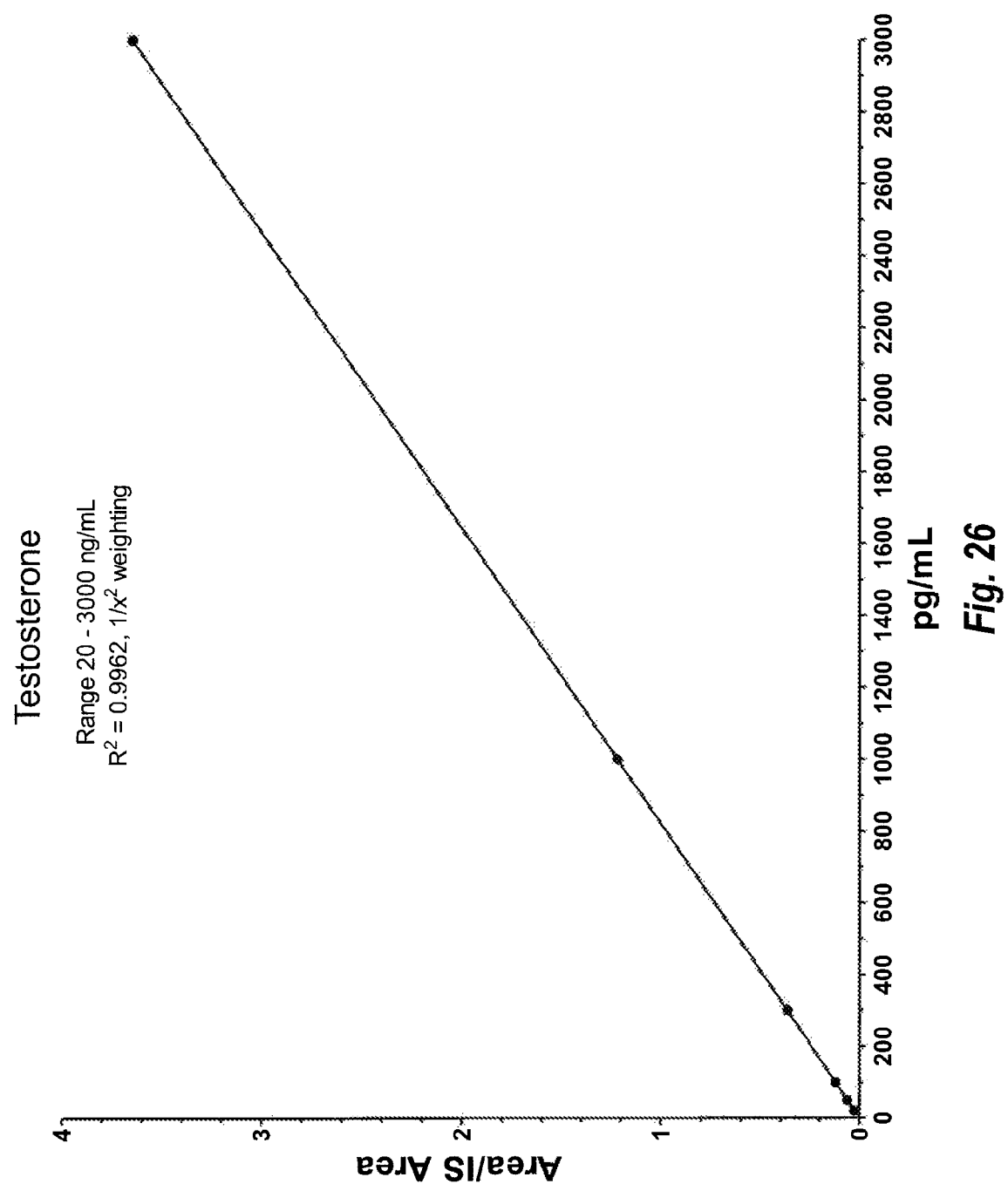
FIG. 26 depicts a standard curve for testosterone in antibody-stripped serum.

Comparison of full scan data for the [M+H]+ ion using ammonium formate in the mobile phase verses the [M+H—$H_2O$]+ for Vitamin $D_2$, for example, using formic acid in the mobile phase are shown in the FIGS. 4A-4B. Note that the addition of an ammonium source significantly increases the sensitivity of detection and significantly improves the signal-to-noise ratio. Note also that the [M+H]+ ion is not detected without ammonium ions.

More important to the quantitation using MS/MS is the comparison of the SRM data from using the [M+H]+ and [M+H—$H_2O$]+ as the precursor ions. Those comparisons are shown for 25-OH $D_2$ in FIGS. 5A and 5B. It is clear that the use of the [M+H]+ ion formed by the presence of ammonium ions in the mobile by electrospray has higher sensitivity then using the [M+H—$H_2O$]+ ion by APCI. The data in FIGS. 5A and 5B illustrate that detection and quantitation of 25-hydroxyvitamin $D_2$ with the [M+H]+ ion from ESI is about 3.5 times more sensitive than detection with the [M+H—$H_2O$]+ from APCI.

Further discussion of LC-MS purification and analysis of vitamin D metabolites can be found in U.S. Prov. Pat. App. Ser. No. 61/408,385 entitled "LC-MS SEPARATION AND DETECTION OF VITAMIN D METABOLITES" filed 29 Oct. 2010 with inventors Joseph L. Herman and Dayana Argoti, the entirety of which is incorporated herein by reference.

Example 2

Purification and Analysis of Analytes of Interest in Neat Samples and Serum

FIGS. 6-15 depict MRM chromatograms illustrating purification and analysis of 40 separate analytes of interest in neat samples on a Cyclone P clean-up column followed by a Hypersil Gold PFP analytical column. Isocratic runs of varying amounts of organic mobile phase were used to characterize the retentive properties of each analyte. Based on the these results the final mobile phases chosen were Solution A: 10 mM ammonium formate, 0.01% formic acid, water and Solution B: 10 mM ammonium formate, 0.01% formic acid, methanol. FIGS. 6-15 illustrate that baseline separation of compounds having hydrophobicities ranging across about 7 log Ps can be achieved using the methods, systems, and kits described herein. It was unexpected that compounds so widely ranging in log Ps could be separated using the methods systems and kits described herein. The only parameters that were varied across the various compounds were LC run parameters (e.g., flow rate, ratios of one buffer to another, temperature, and the like) and MS system parameters (e.g., ionization voltage, desolvation temperature, and the like). Columns and buffers were not changed.

FIGS. 16-20 depict MRM chromatograms illustrating purification and analysis of a number of separate analytes of interest ranging in log P from about 0.1 (norcodeine) to about 5.01 (everolimus). The analytes of interest were dissolved in antibody stripped human serum and purified on a Cyclone P clean-up column followed by an Accucore PFP™ analytical column. Based on these results, the final mobile phases identified above (i.e., Solution A: 10 mM ammonium formate, 0.01% formic acid, water and Solution B: 10 mM ammonium formate, 0.01% formic acid, methanol) were shown to be effective under these conditions. For the analytes of interest illustrated in FIGS. 16-20, no recovery or matrix effects (i.e., interference from the matrix as compared to "neat" samples) were detected. In addition, comparing FIGS. 11 and 20, for example, it can be seen that the antibody stripped human serum, Cyclone P clean-up column, and Accucore PFP™ analytical column can provide better separation than seen with "neat" samples separated with a Cyclone P clean-up column followed by a Hypersil Gold PFP analytical column. As with FIGS. 6-15, the only parameters that were varied across the various compounds illustrated in FIGS. 16-20 were LC run parameters (e.g., flow rate, ratios of one buffer to another, temperature, and the like) and MS system parameters (e.g., ionization voltage, desolvation temperature, and the like). Columns and buffers were not changed.

Referring now to Table 2, additional data regarding the analytes of interest are illustrated. The compounds listed in table 2 can be analyzed by LC-MS for a variety of clinical and drug monitoring purposes using the methods, systems, and kits described herein. The compounds listed in Table 2 have log Ps ranging from about −1.2 (busulfan) to about 6 (25OH vitamin $D_2$), which represents a difference in hydrophobicity over slightly more than about seven orders of magnitude.

Table 2 also shows the lower and upper clinical reference ranges for many of the compounds listed in Table 2 in the "Low" and "High" columns, respectively, and the approximate limit of quantitation (LOQ) using the methods, systems, apparatuses, and kits described herein. The lower and upper clinical reference ranges represent the dynamic range for each of the compounds expected for the compounds in a clinical context. In essentially all cases, however, the limits of detection and the LOQs are much lower than the lower clinical reference range.

The LOQs listed in Table 2 range from a high of about 50 ng/mL for the amphetamines to a low of about 10 pg/mL for some of the steroids. This is at least as good as and in some cases far better than the LOQs for currently practiced methods that have been optimized for each analyte. However, methods that have been optimized for each separate analyte cannot be adapted for purification and analysis of analytes having differences in hydrophobicity over slightly more than about seven orders of magnitude. That is, a typical LC-MS method that is optimized for an analyte or a class of analytes such as vitamin D metabolites is can generally only be used for purification and analysis of that particular analyte or class of analytes. In contrast, the methods, kits, systems, and apparatuses described herein are useful for purification and analysis of analytes having differences in hydrophobicity over slightly more than about seven orders of magnitude. In addition, it was observed, quite unexpectedly, that electrospray ionization (ESI) improved sensitivity relative to atmospheric pressure chemical ionization (APCI), for many of the analytes tested using the methods systems and kits described herein (Table 2). APCI is recognized as the accepted method of ionization for many common analytes of interest.

TABLE 2

| Endocrinology | | | | | | |
|---|---|---|---|---|---|---|
| Vitamin D | logP | Low | High | Units | Approx [LOQ] | ESI/APCI |
| 25OH vitamin D2 | 5.69 | 10 | 65 | ng/mL | 10 ng/mL | 8.81 |
| 25OH vitamin D3 | 5.61 | | | | 10 ng/mL | 3.32 |

| | logP | Low | High | Units | Approx [LOQ] | ESI/APCI |
|---|---|---|---|---|---|---|
| Steroids | | | | | | |
| Testosterone | 4.44 | 0.01 | 10 | ng/mL | 50 pg/mL | 16.4 |
| Cortisol (hydrocortisone) | 1.26 | 1 | 70 | μg/day | 50 pg/mL | 54.5 |
| Cortisone | 1.58 | | | | 50 pg/mL | 35.4 |
| Progesterone | 3.58 | | | | 10 pg/mL | |
| Hydroxyprogesterone | 3.52 | | | | 10 pg/mL | |
| Prednisone | 2.07 | | | | 10 pg/mL | |
| Androstenedione | 2.93 | | | | 10 pg/mL | |
| Therapeutic Drug Monitoring | | | | | | |
| Immunosuppressants | | | | | | |
| Tacrolimus | 3.3 | 1 | 30 | ng/mL | 50 pg/mL | 21.7 |
| Everolimus | 5.01 | 0.3 | 200 | ng/mL | 50 pg/mL | 29.2 |
| Sirolimus | 4.3 | 0.3 | 200 | ng/mL | 50 pg/mL | 27.3 |
| Cyclosporine A | 4.12 | 5 | 1000 | ng/mL | 500 pg/mL | 9.52 |
| Chemotherapeutics | | | | | | |
| Methotrexate | 0.94 | 1 | 1000 | ng/mL | 500 pg/mL | |
| Busulfan | −1.15 | 5 | 2000 | ng/mL | 1 ng/mL | |
| 5-Fluorouracil | −0.9 | 0.01 | 1 | ng/mL | | |
| Docetaxel | 2.4 | 1 | 1000 | ng/mL | 500 pg/mL | |
| Pain management & Drugs of Abuse | | | | | | |
| NIDA 5 | | | | | | |
| Phencyclidine | 4.14 | | | | 0.5 ng/mL | |
| Benzoylecgonine | 1.64 | 5 | 2500 | ng/mL | 0.05 ng/mL | 12.2 |
| Cocaine | 1.91 | | | | 0.05 ng/mL | 16 |
| Delta9-THC | 5.53 | | | | 5 ng/mL | 0.75 |
| 11-norDelta-9-THC-COOH | 4.6 | 10 | 1250 | ng/mL | 5 ng/mL | 0.53 |
| Amphetamines | | | | | | |
| Amphetamine | 1.7 | 51 | 5000 | ng/mL | 50 ng/mL | |
| Methamphetamine | 2.2 | 51 | 5000 | ng/mL | 50 ng/mL | |
| MDMA | 1.98 | 51 | 5000 | ng/mL | 50 ng/mL | |
| MDEA | 2.31 | 51 | 5000 | ng/ml | 50 ng/mL | |
| MDA | 1.46 | 51 | 5000 | ng/ml | 50 ng/ml | |
| Opiates/Opioids | | | | | | |
| Hydromorphone | 1 | 5 | 1000 | ng/mL | 2 ng/mL | |
| Norhydrocodone | 0.89 | | | | 2 ng/mL | |
| Norcodeine | 1.07 | | | | 2 ng/mL | |
| Morphine | 1.73 | 25 | 1000 | ng/mL | 20 ng/mL | |
| Hydrocodone | 1.27 | 2 | 1000 | ng/mL | 2 ng/mL | |
| Codeine | 1.45 | 2 | 1000 | ng/mL | 2 ng/mL | |
| Noroxycodone | 0.1 | | | | 2 ng/mL | |
| Oxymorphone | 0.21 | 5 | 1000 | ng/mL | 20 ng/mL | |
| Dihydrocodeine | 1.63 | 5 | 1000 | ng/mL | 0.2 ng/mL | |
| Oxycodone | 0.48 | 5 | 1000 | ng/mL | 2 ng/mL | |
| 6-MAM | 1.81 | | | | 2 ng/mL | |
| Tapentadol | 3.43 | | | | 0.5 ng/mL | 7.1 |
| Norfentanyl | 3.94 | 0.5 | 200 | ng/mL | 0.05 ng/mL | 10.3 |

TABLE 2-continued

| Fentanyl | 4.59 | 0.5 | 200 | ng/mL | 0.05 | ng/mL | 3.3 |
| Tramadol | 2.53 | | | | 5 | ng/mL | |
| Methadone | 4.55 | | | | 5 | ng/mL | 14.5 |
| Metoprolol | 2.18 | | | | 0.05 | ng/mL | 8.7 |

Example 3

Performance of Immunosuppressant Drugs, 25-Hydroxy Vitamin $D_2$ and $D_3$, and Chemotherapeutics in Biological Matrix Solution FIGS. 21-26 illustrate the performance of immunosuppressant drugs, 25-hydroxy vitamin $D_2$ and $D_3$, and the chemotherapeutic drugs docetaxcel and busulfin in matrix (e.g., blood or serum). No recovery or matrix effects (i.e., interference from the matrix as compared to "neat" samples) were detected for the immunosuppressant drugs, 25-hydroxy vitamin $D_2$ and $D_3$, docetaxel or busulfan in biological matrix solution. It is interesting to note that busulfin (log $P \approx -1.15$) and 25-hydroxy vitamin $D_2$ (log $P \approx 5.69$) represent the lower and upper log P ranges for analytes tested using the methods described herein. It was unexpected that compounds as different as busulfin and 25-hydroxy vitamin $D_2$ could be separated using the methods systems and kits described herein. The only parameters that were varied from busulfin to 25-hydroxy vitamin $D_2$ were LC run parameters (e.g., flow rate, ratios of one buffer to another, temperature, and the like) and MS system parameters (e.g., ionization voltage, desolvation temperature, and the like). Columns and buffers were not changed.

Example 4

Method Details for Purification and Analysis of the Analytes of Interest

Tables 3-11 illustrate various method details for purification and analysis of the various analytes of interest discussed herein.

TABLE 3

| System set-up/configuration | |
|---|---|
| Data Window Start | 20 |
| Data Window Length | 359 |
| Column One | Cyclone P |
| Column Two | Hypersil Gold PFP or Accucore PFP |
| Method Comment | |
| Loading Pump | Quaternary Pump |
| Solvent A | 10 mM AmmFormt/0.01% FA $H_2O$ |
| Solvent B | 10 mM AmmFormt/0.01% FA 95:5 ACN:$H_2O$ |
| Solvent C | 45/45/10 IPA/ACN/Acetone |
| Solvent D | 10 mM AmmFormt/0.01% FA MeOH |
| Eluting Pump | Quaternary Pump |
| Solvent A | 10 mM AmmFormt/0.01% FA $H_2O$ |
| Solvent B | 10 mM AmmFormt/0.01% FA 95:5 ACN:$H_2O$ |
| Solvent C | 45/45/10 IPA/ACN/Acetone |
| Solvent D | 10 mM AmmFormt/0.01% FA MeOH |

TABLE 4

LC Gradient details for ISDs, Steroids and Drugs of Abuse

| | | | Loading | | | | | | | | Eluting | | | | | | |
|---|---|---|---|---|---|---|---|---|---|---|---|---|---|---|---|---|---|
| Step | Start | Sec | Flow | Grad | % A | % B | % C | % D | Tee | Loop | Flow | Grad | % A | % B | % C | % D | Comment |
| 1 | 0:00 | 25 | 1.50 | Step | 100 | | | | ~~~ | out | 0.50 | Step | 100 | | | | Sample clean-up |
| 2 | 0:25 | 5 | 0.10 | Step | 100 | | | | ~~~ | out | 0.35 | Step | 100 | | | | Lower flow rate |
| 3 | 0:30 | 60 | 0.10 | Step | | | | 100 | T | in | 0.35 | Step | 100 | | | | Transfer |
| 4 | 2:00 | 60 | 1.50 | Step | | | | 100 | T | in | 0.35 | Ramp | | | | 100 | Loop fill/Grad Elute |
| 5 | 2:15 | 30 | 1.50 | Step | | | | 100 | ~~~ | in | 0.50 | Step | | | | 100 | Loop fill/Grad Elute |
| 6 | 2:30 | 30 | 1.50 | Step | | | 100 | | ~~~ | out | 0.50 | Ramp | 100 | | | | TFC Wash |
| 7 | 2:45 | 90 | 1.50 | Step | 100 | | | | ~~~ | out | 0.50 | Ramp | 100 | | | | Equilibrate |

TABLE 5

LC Gradient details for Opiates

| | | | Loading | | | | | | | | Eluting | | | | | | |
|---|---|---|---|---|---|---|---|---|---|---|---|---|---|---|---|---|---|
| Step | Start | Sec | Flow | Grad | % A | % B | % C | % D | Tee | Loop | Flow | Grad | % A | % B | % C | % D | Comment |
| 1 | 0:00 | 25 | 1.50 | Step | 100 | | | | ~~~ | out | 0.70 | Step | 100 | | | | Sample clean-up |
| 2 | 0:25 | 5 | 0.10 | Step | 100 | | | | ~~~ | out | 0.50 | Step | 100 | | | | Lower flow rate |
| 3 | 0:30 | 90 | 0.10 | Step | 100 | | | | | T | in | 0.50 | Step | 100 | | | Transfer |
| 4 | 2:00 | 15 | 1.50 | Step | 50 | | | 50 | | in | 0.50 | Ramp | 84 | | | 16 | Loop fill/Grad Elute |
| 5 | 2:15 | 15 | 1.50 | Step | 50 | | | 50 | | in | 0.50 | Ramp | 67 | | | 33 | Loop fill/Grad Elute |
| 6 | 2:30 | 15 | 1.50 | Step | | | 100 | | | out | 0.50 | Ramp | 50 | | | 50 | TFC Wash/Grad Elute |
| 7 | 2:45 | 15 | 1.50 | Step | | | 100 | | | out | 0.50 | Ramp | 34 | | | 66 | TFC Wash/Grad Elute |
| 8 | 3:00 | 15 | 1.50 | Step | | | | 100 | | out | 0.50 | Ramp | 18 | | | 82 | TFC Wash/Grad Elute |
| 9 | 3:15 | 15 | 1.50 | Step | | | | 100 | | out | 0.50 | Ramp | ~ | | | 100 | TFC Wash/Grad Elute |
| 10 | 3:30 | 110 | 1.50 | Step | 100 | | | | | out | 0.50 | Step | 100 | | | | Equilibrate |
| 11 | 5:20 | 60 | 1.50 | Step | 100 | | | | | out | 0.70 | Step | 100 | | | | Equilibrate |

TABLE 6

LC Gradient details for Amphetamines

| | | | Loading | | | | | | | | Eluting | | | | | | |
|---|---|---|---|---|---|---|---|---|---|---|---|---|---|---|---|---|---|
| Step | Start | Sec | Flow | Grad | % A | % B | % C | % D | Tee | Loop | Flow | Grad | % A | % B | % C | % D | Comment |
| 1 | 0:00 | 25 | 1.50 | Step | 100 | | | | ~~~~ | out | 0.70 | Step | 100 | | | | Sample clean-up |
| 2 | 0:25 | 5 | 0.10 | Step | 100 | | | | ~~~~ | out | 0.50 | Step | 100 | | | | Lower flow rate |
| 3 | 0:30 | 90 | 0.10 | Step | 100 | | | | T | in | 0.50 | Step | 100 | | | | Transfer |
| 4 | 2:00 | 30 | 1.50 | Step | 50 | | | 50 | | in | 0.50 | Ramp | 84 | | | 16 | Loop fill/Grad Elute |
| 5 | 2:30 | 30 | 1.50 | Step | 50 | | | 50 | | in | 0.50 | Ramp | 67 | | | 33 | Loop fill/Grad Elute |
| 6 | 3:00 | 30 | 1.50 | Step | | | 100 | | | out | 0.50 | Ramp | 50 | | | 50 | TFC Wash/Grad Elute |
| 7 | 3:30 | 30 | 1.50 | Step | | | 100 | | | out | 0.50 | Ramp | 34 | | | 66 | TFC Wash/Grad Elute |
| 8 | 4:00 | 30 | 1.50 | Step | | | | 100 | | out | 0.50 | Ramp | 18 | | | 82 | TFC Wash/Grad Elute |
| 9 | 4:30 | 30 | 1.50 | Step | | | | 100 | | out | 0.50 | Ramp | ~ | | | 100 | TFC Wash/Grad Elute |
| 10 | 5:00 | 110 | 1.50 | Step | 100 | | | | | out | 0.50 | Step | 100 | | | | Equilibrate |
| 11 | 6:50 | 60 | 1.50 | Step | 100 | | | | | out | 0.70 | Step | 100 | | | | Equilibrate |

TABLE 7

LC Gradient details for Vitamin D metabolites

| | | | Loading | | | | | | | | Eluting | | | | | | |
|---|---|---|---|---|---|---|---|---|---|---|---|---|---|---|---|---|---|
| Step | Start | Sec | Flow | Grad | % A | % B | % C | % D | Tee | Loop | Flow | Grad | % A | % B | % C | % D | Comment |
| 1 | 0:00 | 30 | 1.50 | Step | 80 | | | 20 | ~~~~ | out | 0.50 | Step | 80 | | | 20 | Sample clean-up |
| 2 | 0:30 | 90 | 0.10 | Step | 80 | | | 20 | T | in | 0.40 | Step | 80 | | | 20 | Transfer |
| 3 | 2:00 | 60 | 0.10 | Step | | | 100 | | ~~~~ | in | 0.50 | Ramp | 5 | | | 95 | TFC Wash/Grad Elute |
| 4 | 3:00 | 60 | 1.50 | Step | | | | 100 | ~~~~ | in | 0.50 | Step | 5 | | | 95 | Loop fill/Grad Elute |
| 5 | 4:00 | 120 | 1.20 | Step | 80 | | | 20 | ~~~~ | out | 0.50 | Step | 80 | | | 20 | Equilibrate |

TABLE 8

MS Conditions for Immunosuppressants

| | |
|---|---|
| Spray voltage | 4500 |
| Vaporizer Temperature | 350 |
| Sheath Gas | 60 |
| Aux gas | 35 |
| Capillary Temperature | 200 |
| S-lens amplitude | 55 |

TABLE 9

MS Conditions for Vitamin D Metabolites

| | |
|---|---|
| Spray voltage | 5000 |
| Vaporizer Temperature | 400 |
| Sheath Gas | 60 |
| Aux gas | 35 |
| Capillary Temperature | 199 |

TABLE 10

MS Acquisition Settings for Vitamin D Metabolites (Ion Monitoring: SRM)

| Analyte | Precursor Ion (Q1) | Product Ions (Q3) | Collision Energy | S-lens |
|---|---|---|---|---|
| Vitamin D2 | 413.353 | 91.098 | 55 | 87 |
| | | 95.158 | 33 | 87 |
| | | 105.104 | 42 | 87 |
| | | 159.149 | 28 | 87 |
| Vitamin D3 | 401.352 | 91.122 | 50 | 87 |
| | | 105.133 | 36 | 87 |
| | | 159.139 | 24 | 87 |
| | | 365.425 | 10 | 87 |

TABLE 10-continued

MS Acquisition Settings for Vitamin D Metabolites (Ion Monitoring: SRM)

| Analyte | Precursor Ion (Q1) | Product Ions (Q3) | Collision Energy | S-lens |
|---|---|---|---|---|
| d6-Vitamin D3 | 407.380 | 107.115 | 30 | 87 |
| | | 133.105 | 31 | 87 |
| | | 147.199 | 27 | 87 |
| | | 159.190 | 27 | 87 |

TABLE 11

Acquisition Method Parameters for Vitamin D Metabolites

| | |
|---|---|
| Scan width (m/z) | 0.01 |
| Scan time (s) | 0.05 |
| Peak width (Q1) | 0.2 |
| Peak width (Q3) | 0.7 |
| Chrom peak filter width | 10 |
| Collision Pressure | 1.5 |

Referring to Tables 4-7, it was found that selecting the amount of organic in the transfer loop of valve one (what it takes to get compounds off the turboflow column in a reasonable time frame), created significant efficiency in transfer, because the loop was optimally pre-loaded. It was also found that this value is unique to each class of compounds.

Likewise, referring to Tables 4-7, it was also found that the ratio of the flow rates between the clean-up elution step (i.e., the turbulent flow chromatography elution step) and the analytical column loading step (the whole thing can be called the transfer step) was optimized per individual compound class to ensure that everything eluting from the clean-up column was focused on the head of the analytical column (i.e., no analytical elution during the transfer step). This was found to significantly improve recovery and analytical peak shape.

Likewise, referring to Tables 4-7, it was also found that the analytical elution step could be optimized for each compound class to separate isobaric interferences, cross-talk between compounds, and matrix interferences.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method, comprising:
   providing a fluid biological sample containing two or more analytes, the two or more analytes comprising at least one analyte selected from a first group and at least one analyte selected from a second group, wherein respective log partition coefficient (log P) values of the two or more analytes are separated by at least 4.5 log P units, the two or more analytes having respective log P values within the range of about −1.2 to about 6;
   providing a liquid chromatography-mass spectrometry (LC-MS) system, comprising:
      a liquid chromatography system, comprising a single analytical liquid chromatography column, a single sample clean-up liquid chromatography column in fluid communication with and upstream of the single analytical liquid chromatography column, one aqueous mobile phase buffer solution, and one organic or non-aqueous mobile phase buffer solution, wherein the one aqueous mobile phase buffer solution and the one organic or non-aqueous mobile phase buffer solution each include a source of ammonium ions, wherein the source of ammonium ions is ammonium formate or ammonium acetate; and
      a mass spectrometer,
   purifying the two or more analytes using the single sample clean-up liquid chromatography column, the single analytical liquid chromatography column, the one aqueous mobile phase buffer solution, and the one organic or non-aqueous mobile phase buffer solution by varying at least one liquid chromatography system parameter selected from the group consisting of mobile phase buffer flow rate, a ratio of an aqueous mobile phase buffer solution to a non-aqueous mobile phase buffer solution, a gradient varying ratios of the aqueous and non-aqueous mobile phase buffer solutions, and combinations thereof; and
   analyzing the two or more analytes using the mass spectrometer by varying at least one mass spectrometry system parameter selected from the group consisting of ionization voltage, desolvation temperature, electrode voltage, collision gas temperature, collision gas pressure, collision energy, and combinations thereof.

2. The method of claim 1, wherein the liquid chromatography system further comprises a control system configured to control or vary the at least one liquid chromatography system parameter, the method further comprising selecting at least one analysis protocol based on the two or more analytes, wherein selecting the at least one analysis protocol includes varying the at least one liquid chromatography system parameter to purify the two or more analytes without making column or buffer changes, wherein the at least one analysis protocol comprise pre-set system parameters for chromatographic separation and mass spectrometric analysis of the two or more analytes, wherein the pre-set system parameters are configured for chromatographic separation and mass spectrometric analysis of analytes selected from the first group and the second group spanning the log P range of −1.2 to 6.

3. The method of claim 1, wherein the fluid biological sample contains a first analyte, a second analyte, and a third analyte, wherein the first analyte has a log P in a range of about −1.2 to about 0, the second analyte has a log P in a range from about 0 to about 5, and the third analyte has a log P greater than about 5 and less than or equal to about 6.

4. The method of claim 1, wherein the two or more analytes are separated by 4.5 to about 6 log P units.

5. The method of claim 1, wherein the two or more analytes are separated by about 6 to about 7 log P units.

6. The method of claim 1, wherein the two or more analytes include vitamin D or a metabolite or derivative thereof.

7. The method of claim 1, wherein the two or more analytes are selected from vitamin D, steroid hormones, protein hormones, proteins, peptide hormones, peptides, bacterial toxins, immunosuppressants, chemotherapeutics, tricyclic antidepressants, azole antifungals, anti-epileptics, anti-retrovirals, opiates and/or opioids, drugs of abuse, barbiturates, benzodiazepines, metabolites thereof, and combinations thereof.

8. The method of claim 1, wherein the two or more analytes include 25-hydroxy vitamin $D_2$ and busulfan.

9. The method of claim 1, wherein the two or more analytes include 25-hydroxy vitamin $D_2$ or 25-hydroxyvitamin $D_3$.

10. The method of claim 1, wherein the two or more analytes include a chemotherapeutic agent.

11. The method of claim 1, wherein the chemotherapeutic agent is selected from the group consisting of busulfan, 5-fluorouracil, methotrexate.

12. The method of claim 1, wherein the organic or non-aqueous mobile phase buffer solution comprises 10 mM ammonium formate with 0.01% formic acid in methanol.

13. The method of claim 1, wherein the aqueous mobile phase buffer solution comprises 10 mM ammonium formate with 0.01% formic acid in water.

14. The method of claim 1, wherein purifying the two or more analytes comprises:
   introducing the two or more analytes into the single sample clean-up liquid chromatography column;
   eluting the two or more analytes from the single sample clean-up liquid chromatography column onto the single analytical liquid chromatography column; and
   eluting the two or more analytes from the single analytical liquid chromatography column into the mass spectrometer,
   wherein each of the foregoing is performed with one or both of the one aqueous mobile phase buffer solution and the one organic or non-aqueous mobile phase buffer solution.

15. The method of claim 1, wherein the two or more analytes are eluted from the single analytical liquid chromatography column with a gradient of the organic or non-aqueous mobile phase buffer solution to the aqueous mobile phase buffer solution.

16. A method, comprising:
purifying two or more analytes contained in a fluid biological sample using a liquid chromatography system of a liquid chromatography-mass spectrometry (LC-MS) system by varying at least one liquid chromatography system parameter selected from the group consisting of mobile phase buffer flow rate, a ratio of aqueous mobile phase buffer solution to organic or non-aqueous mobile phase buffer solution, a gradient varying ratios of the aqueous mobile phase buffer solution and the organic or non-aqueous mobile phase buffer solution, and combinations thereof, the liquid chromatography system comprising:
a single analytical liquid chromatography column;
a single sample clean-up liquid chromatography column in fluid communication with and upstream of the single analytical liquid chromatography column;
one aqueous mobile phase buffer solution comprising ammonium formate or ammonium acetate; and
one organic or non-aqueous mobile phase buffer solution comprising ammonium formate or ammonium acetate,
the two or more analytes having respective log partition coefficient (log P) values within a range of about −1.2 to about 6 and separated by at least 4.5 log P units; and
analyzing the two or more analytes using a mass spectrometer of the liquid chromatography-mass spectrometry (LC-MS) system by varying at least one mass spectrometry system parameter selected from the group consisting of ionization voltage, desolvation temperature, electrode voltage, collision gas temperature, collision gas pressure, collision energy, and combinations thereof.

17. The method of claim 16, wherein the fluid biological sample contains a first analyte, a second analyte, and a third analyte, wherein the first analyte has a log P in a range of about −1.2 to about 0, the second analyte has a log P in a range from about 0 to about 5, and the third analyte has a log P greater than about 5 and less than or equal to about 6.

18. The method of claim 16, wherein the two or more analytes are separated by 4.5 to about 6 log P units.

19. The method of claim 16, wherein the two or more analytes are separated by about 6 to about 7 log P units.

20. The method of claim 16, wherein the two or more analytes are separated by at least 6.84 log P units.

21. The method of claim 16, wherein the two or more analytes are selected from vitamin D, steroid hormones, protein hormones, proteins, peptide hormones, peptides, bacterial toxins, immunosuppressants, chemotherapeutics, tricyclic antidepressants, azole antifungals, anti-epileptics, anti-retrovirals, opiates and/or opioids, drugs of abuse, barbiturates, benzodiazepines, metabolites thereof, and combinations thereof.

22. The method of claim 16, wherein the two or more analytes include 25-hydroxy vitamin $D_2$ and busulfan.

23. The method of claim 16, wherein the two or more analytes include 25-hydroxy vitamin $D_2$ or 25-hydroxyvitamin $D_3$.

24. The method of claim 16, wherein:
the one aqueous mobile phase buffer solution comprises:
water;
ammonium formate or ammonium acetate; and
an acid, and
the one organic or non-aqueous mobile phase buffer solution comprises:
an organic phase;
ammonium formate or ammonium acetate; and
an acid.

25. The method of claim 16, wherein the acid in the one aqueous mobile phase buffer solution and the acid in the one non-aqueous mobile phase buffer solution is formic acid.

26. The method of claim 16, wherein the organic phase is selected from the group consisting of methanol, acetonitrile, ethanol, isopropanol, and combinations thereof.

27. The method of claim 16, wherein the organic or non-aqueous mobile phase buffer solution comprises 10 mM ammonium formate with 0.01% formic acid in methanol.

28. The method of claim 16, wherein the aqueous mobile phase buffer solution comprises 10 mM ammonium formate with 0.01% formic acid in water.

29. The method of claim 16, wherein purifying the two or more analytes comprises:
introducing the two or more analytes into the single sample clean-up liquid chromatography column;
eluting the two or more analytes from the single sample clean-up liquid chromatography column onto the single analytical liquid chromatography column; and
eluting the two or more analytes from the single analytical liquid chromatography column into the mass spectrometer,
wherein each of the foregoing is performed with one or both of the one aqueous mobile phase buffer solution and the one organic or non-aqueous mobile phase buffer solution.

30. The method of claim 16, wherein the two or more analytes are eluted from the single analytical liquid chromatography column with a gradient of the organic or non-aqueous mobile phase buffer solution to the aqueous mobile phase buffer solution.

31. The method of claim 16, wherein the liquid chromatography system is selected from the group consisting of high-performance liquid chromatography (HPLC), ultra high-performance liquid chromatography (UHPLC), high turbulence liquid chromatography (HTLC), and combinations thereof.

32. The method of claim 16, wherein the two or more analytes include a chemotherapeutic agent.

33. The method of claim 32, wherein the chemotherapeutic agent is selected from the group consisting of busulfan, 5-fluorouracil, methotrexate.

34. The method of claim 16, wherein the liquid chromatography system further comprises a control system linked to each of the liquid chromatography system and the mass spectrometer, the method further comprising selecting at least one analysis protocol using the control system and based on the two or more analytes, the at least one analysis protocol comprising pre-set system parameters for chromatographic separation of the two or more analytes by varying the at least one liquid chromatography system parameter to purify the two or more analytes without making column or buffer changes and pre-set system parameters for mass spectrometric analysis of the two or more analytes.

35. The method of claim 34, wherein the pre-set system parameters for mass spectrometric analysis include varying at least one mass spectrometry system parameter without making hardware configuration changes.

36. The method of claim 34, wherein the LC-MS system further comprises one or more of:
a sample handling device operably coupled to the control system; and a sample detection device operably coupled to at least one of the sample handling device and the control system.

37. A method, comprising:

purifying two or more analytes contained in a fluid biological sample using a liquid chromatography system of a liquid chromatography-mass spectrometry (LC-MS) system, the liquid chromatography system comprising:
- a single analytical liquid chromatography column;
- a single sample clean-up liquid chromatography column in fluid communication with and upstream of the single analytical liquid chromatography column;
- one aqueous mobile phase buffer solution comprising ammonium formate or ammonium acetate; and
- one organic or non-aqueous mobile phase buffer solution comprising ammonium formate or ammonium acetate, the two or more analytes having respective log partition coefficient (log P) values within a range of about −1.2 to about 6 and separated by at least 4.5 log P units, wherein purifying the two or more analytes comprises varying at least one liquid chromatography system parameter selected from the group consisting of mobile phase buffer flow rate, a ratio of aqueous mobile phase buffer solution to organic or non-aqueous mobile phase buffer solution, a gradient varying ratios of the aqueous mobile phase buffer solution and the organic or non-aqueous mobile phase buffer solution, and combinations thereof; and analyzing the two or more analytes using a mass spectrometer of the liquid chromatography-mass spectrometry (LC-MS) system by varying at least one mass spectrometry system parameter selected from the group consisting of ionization voltage, desolvation temperature, electrode voltage, collision gas temperature, collision gas pressure, collision energy, and combinations thereof.

* * * * *